United States Patent [19]

Young et al.

[11] Patent Number: 4,962,203
[45] Date of Patent: Oct. 9, 1990

[54] 2-SUBSTITUTED QUINOLINES USEFUL AS LEUKOTRIENE ANTAGONISTS

[75] Inventors: Robert N. Young, Quebec; Haydn W. R. Williams; Serge Leger, both of Dollard des Ormeaux; Richard Frenette, Laval; Robert Zamboni, Longueuil, all of Canada

[73] Assignee: Merck Frost Canada, Inc., Kirkland, Canada

[21] Appl. No.: 393,436

[22] Filed: Aug. 14, 1989

Related U.S. Application Data

[63] Continuation of Ser. No. 253,993, Oct. 5, 1988, abandoned, which is a continuation of Ser. No. 874,243, Jun. 13, 1986, abandoned, which is a continuation-in-part of Ser. No. 746,204, Jun. 18, 1985, abandoned.

[51] Int. Cl.$^5$ .................... C07D 215/18; A61K 31/47
[52] U.S. Cl. .................................... 546/180; 514/311; 514/312; 514/314; 546/152; 546/153; 546/157; 546/174; 546/176; 546/181; 546/14
[58] Field of Search .............. 546/152, 153, 157, 180, 546/181, 176, 174; 514/311, 312, 314

[56] References Cited

U.S. PATENT DOCUMENTS

| | | | |
|---|---|---|---|
| Re. 31,624 | 7/1984 | Dewhirst | 546/152 |
| 4,444,584 | 4/1984 | Serban | 546/153 |
| 4,567,184 | 1/1986 | Musser | 546/152 |
| 4,598,150 | 7/1986 | Fujisaki | 546/152 |
| 4,631,287 | 12/1986 | Chakraborty | 514/311 |
| 4,761,425 | 8/1988 | Girard et al. | 549/401 |
| 4,769,461 | 9/1988 | Musser | 546/155 |
| 4,772,703 | 9/1988 | Musser et al. | 546/152 |
| 4,794,188 | 12/1988 | Musser et al. | 546/152 |
| 4,839,369 | 6/1989 | Youssefyeh | 514/314 |
| 4,851,409 | 7/1989 | Young et al. | 514/228 |

FOREIGN PATENT DOCUMENTS

| | | |
|---|---|---|
| 56398/86 | 10/1986 | Australia. |
| 110405 | 11/1983 | European Pat. Off.. |
| 0206751 | 12/1986 | European Pat. Off.. |
| 0219308 | 4/1987 | European Pat. Off. ............ 546/153 |
| WO87/05510 | 9/1987 | World Int. Prop. O.. |

OTHER PUBLICATIONS

K. G. Gorzinger et al.; Eur. J. Med. Chem. 1985-20, No. 6, pp. 487–491.
Burger, A. *Medicinal Chemistry* 2nd Ed., Interscience, New York (1960) p. 42.
Mahler *Biological Chemistry* 2nd Ed. Harper, New York (1971) p. 636.
Schewe, T in *Advances in Enzymology* vol. 58, pp. 197–201 (1986).
Schewe et al., Adv. in Enzym., 58 192–271 (1986).

*Primary Examiner*—Donald G. Daus
*Attorney, Agent, or Firm*—Gabriel Lopez; Hesna J. Pfeiffer

[57] ABSTRACT

Compounds having the formula:

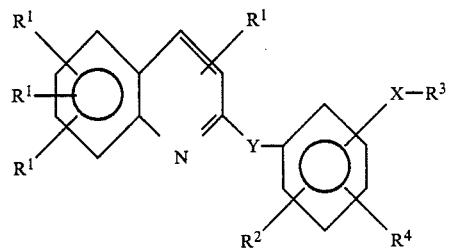

are selective antagonists of leukotrienes of $D_4$. These compounds are useful as anti-asthmatic, anti-allergic, anti-inflammatory, and cytoprotective agents.

9 Claims, No Drawings

2-SUBSTITUTED QUINOLINES USEFUL AS LEUKOTRIENE ANTAGONISTS

CROSS REFERENCE

This is a continuation of Ser. No. 253,993, Oct. 5, 1988, abandoned, which is a continuation of U.S. Ser. No. 068,096, June 29, 1987, abandoned; which is a continuation of U.S. Ser. No. 874,243, June 13, 1986, abandoned; which is a continuation-in-part of U.S. Ser. No. 746,204, June 18, 1985, abandoned.

BACKGROUND OF THE INVENTION

This invention is directed to compounds which act as antagonists of the leukotrienes.

The leukotrienes and their biological activities, especially their roles in various disease states and conditions have been described. For example, see EP No. 140,684 (May 8, 1985), which is incorporated herein by reference.

Several classes of compounds exhibit ability to antagonize the action of leukotrienes in mammals, especially humans. See for example: United Kingdom Patent Specification Nos. 2,058,785 and 2,094,301; and European Patent Application Nos. 56,172, 61,800 and 68,739.

EP No. 110,405 (June 13, 1984) describes anti-inflammatory and antiallergic substituted benzenes which are disclosed to be leukotriene inhibitors, i.e., inhibitors of the 5-lipoxygenase pathway.

SUMMARY OF THE INVENTION

The present invention relates to compounds having activity as leukotriene and SRS-A antagonists or inhibitors, to methods for their preparation, to intermediates useful in their preparation and to methods and pharmaceutical formulations for using these compounds in mammals (especially humans).

Because of their activity as leukotriene antagonists or inhibitors, the compounds of the present invention are useful as anti-asthmatic, anti-allergic, and anti-inflammatory agents and are useful in treating allergic rhinitis, allergic conjunctivitis, and chronic bronchitis and for amelioration of skin diseases like psoriasis and atopic eczema. These compounds are also useful to antagonize or inhibit the pathologic actions of leukotrienes on the cardiovascular and vascular systems for example, actions such as result in angina. The compounds are also useful as cytoprotective agents.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatotoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

DETAILED DESCRIPTION

The compounds of this invention are best realized by Formula I:

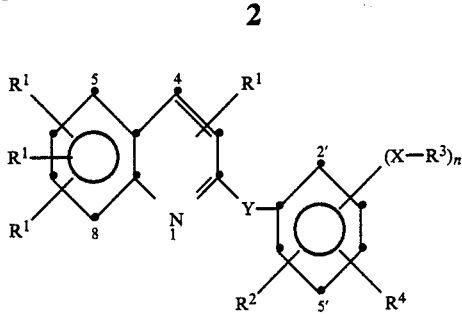

wherein:
$R^1$ is H, halogen, $C_1$-$C_8$ alkyl, $C_2$-$C_8$ alkenyl, $C_2$-$C_8$ alkynyl, —$CR_3$, —$OR^2$, —$SR^2$, —$NR^2R^2$, —CHO, —$COOR^2$, —(C=O)$R^2$, —C(OH)$R^2R^2$, —CN, —$NO_2$, substituted or unsubstituted phenyl, substituted or unsubstituted benzyl, or substituted or unsubstituted phenethyl;
$R^2$ is H, $C_1$-$C_8$ alkyl, $C_2$-$C_8$ alkenyl, $C_2$-$C_8$ alkynyl, —$CF_3$, substituted or unsubstituted phenyl, substituted or unsubstituted benzyl, or substituted or unsubstituted phenethyl;
$R^3$ is —(A)$_m$—(CR$^2$=CR$^2$)$_p$—(CR$^2$R$^2$)$_m$—Q;
$R^4$ is H, halogen, —$NO_2$, —CN, —$OR^2$, —$SR^2$, $NR^2R^2$, or $C_1$-$C_8$ alkyl;
$R^5$ is

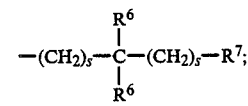

$R^6$ is H or $C_1$-$C_4$ alkyl;
$R^7$ is (A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or
(B) the radical W-$R^8$;
$R^8$ contains up to 21 carbon atoms and is (1) a hydrocarbon radical or (2) an acyl radical of an organic acyclic or monocyclic carboxylic acid containing not more than 1 heteroatom in the ring;
$R^9$ is —$OR^{10}$, —$SR^{10}$, or $NR^{10}R^{10}$;
$R^{10}$ is H, $C_1$-$C_6$ alkyl, —(C=O)$R^{11}$, unsubstituted phenyl or unsubstituted benzyl;
$R^{11}$ is H, $C_1$-$C_8$ alkyl, $C_2$-$C_8$ alkenyl, $C_2$-$C_8$ alkynyl, —$CF_3$, or unsubstituted phenyl, benzyl, or phenethyl;
$R^{12}$ is H, $C_1$-$C_4$ alkyl, or halogen;
m is 0–8;
n is 1 or 2;
p is 0–2;
s is 0–3;
A is —$CR^2R^4$—, or =C=O;
Q is —$COOR^2$, tetrazole, —$COOR^5$, —$COCH_2OH$, —$COHNS(O)_2R^{11}$, —$CH_2OH$, —CN, —$CONR^{10}R^{10}$, —$NHSO_2R^{11}$ (but only when the sum of m and p in $R^3$ is greater than 0), or if is COOH and $R^3$ contains an $R^4$ which is —OH, —SH, or —$NHR^2$ then Q and $R^4$ and the carbons through which they are attached may form a heterocyclic ring with loss of water;
W is O, S, or NH;
X is P, S, —SO, —$SO_2$, or —$NR^2$;

Y is $-(CR^2\!=\!CR^2)_n-$, $-(C\!\equiv\!C)_n-$, $-CR^2R^2-X-$, $-X-CR^2R^2-$, or

with the proviso that when on the carbon adjacent to X it is not OH, SH, or $NHR^2$; and the pharmaceutically acceptable salts thereof.

Alkyl, alkenyl, and alkynyl are intended to include linear, branched, and cyclic structures. Thus, alkyl would include n-butyl, sec-butyl, tert-butyl, cyclobutyl, etc.

Substituted phenyl, benzyl, and phenethyl include 1-2 substituents selected from $C_1$-$C_6$ alkyl, $R^9$, $NO_2$, $SCF_3$, halogen, $-COR^9$, CN, $CF_3$, and $-CHO$.

Halogen includes F, Cl, Br and I.

The prodrug esters of Q (i.e., when $Q=-COOR^5$) are intended to include the esters such as are described by Saari et al., J. Med Chem., 21, No. 8, 746–753 (1978).

When Q and $R^4$ and the carbons through which they are attached from a ring, the rings thus formed include lactones, lactams, and thiolactones.

It is intended that the definitions of any substituent (e.g., $R^1$, $R^2$, m, Q, X, etc.) in a particular molecule is independent of its definitions elsewhere in the molecule. Thus, $-NR^2R^2$ represents $-NHH$, $-NHCH_3$, $-NHC_6H_5$, etc.

Some of the compounds described herein contain one or more centers of asymmetry and may thus give rise to diastereoisomers and optical isomers. The present invention is meant to comprehend such possible diastereoisomers as well as their racemic and resolved, optically active forms.

Preferred compounds of Formula I are best represented by Formula Ia:

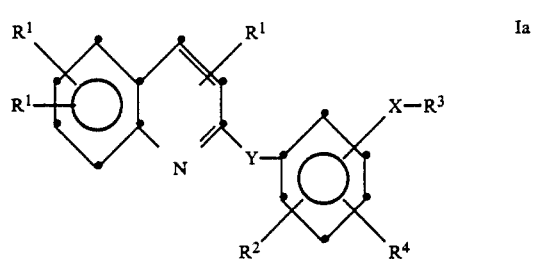

wherein:
$R^1$ is H, halogen, $C_1$-$C_8$ alkyl, $C_2$-$C_8$ alkenyl, $C_2$-$C_8$ alkynyl, $-CF_3$, $-OR^2$, $-SR^2$, $-NR^2R^2$, $-CHO$, $-COOR^2$, $-(C\!=\!O)R^2$, $-C(OH)R^2R^2$, $-CN$, $-NO_2$, substituted or unsubstituted phenyl, substituted or unsubstituted benzyl, or substituted or unsubstituted phenethyl;

Y is $-(CR^2\!=\!CR^2)_n-$ or $-(C\!\equiv\!C)_n-$; $R^2$ to $R^{11}$, m, n, p, s, A, Q, W, and X are as defined for Formula I;

and the pharmaceutically acceptable salts thereof.

More-preferred compounds of Formula I are best represented by Formula Ib:

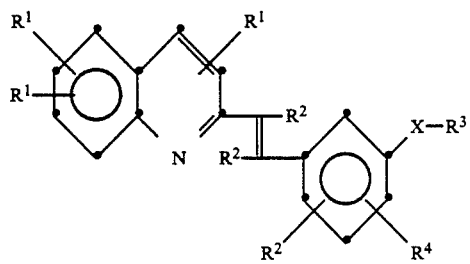

wherein:
$R^1$ is H, halogen, $CH_3$, $-CF_3$, or $SCF_3$;
$R^2$ is H, $C_1$-$C_3$ alkyl, $C_2$-$C_3$ alkenyl, or $-CF_3$;
$R^3$ to $R^{11}$, m, p, s, A, Q, W, and X are as defined for Formula I;

and the pharmaceutically acceptable salts thereof.

Preferred IB compounds are those wherein X is O, $R^3$ is $-(CR^6R^6)_m-Q$, m is 1 to 6, and Q or $COOR^2$, tetrazole, or $CONR^{10}R^{10}$.

Other more-preferred compounds of Formula I are best represented by Formula Ic:

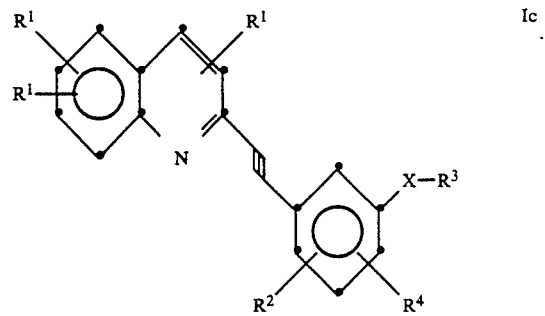

wherein:
$R^1$ is H, halogen, $CH_3$, $C_2$-$C_3$ alkenyl, $-CF_3$, or $SCF_3$;
$R^2$ is H, $C_1$-$C_3$ alkyl, $C_2$-$C_3$ alkenyl, or $-CF_3$;
$R^3$ to $R^{11}$, m, p, s, A, Q, W, and X are as defined for Formula I;

and the pharmaceutically acceptable salts thereof.

Preferred compounds of Ic are those wherein X is O, $R^3$ is $-(CR^6R^6)_m-Q$, m is 1 to 6, and Q is $COOR^2$, tetrazole, or $CONR^{10}R^{10}$.

The compounds of Formula I are active as antagonists of SRS-A and especially of leukotriene $D_4$. These compounds also have modest inhibitory activity on leukotriene biosynthesis but are primarily of therapeutic interest as antagonists. The activity of the compounds of Formulae I can be detected and evaluated by methods known in the art. See for example, Kadin. U.S. Pat. No. 4,296,129.

The ability of the compounds of Formula I to antagonize the effects of the leukotrienes and to inhibit the leukotrienes makes them useful for inhibiting the symptoms induced by the leukotrienes in a human subject. The compounds are valuable therefore in the prevention and treatment of such disease states in which the leukotrienes are the causative factor, e.g. skin disorders, allergic rhinitis, and obstructive airway diseases. The compounds are particularly valuable in the prevention and treatment of allergic bronchial asthma. It will be understood that in this paragraph and in the discussion of methods of treatment which follows, references to the compounds of Formula I are meant to include the pharmaceutically acceptable salts and lactone, lactam or thiolactam forms.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanolinduced lesion assay and (B) an indomethacin-induced ulcer assay and are described in EP No. 140,684.

The magnitude of a prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

The effective daily dosage level for compounds of Formula I inducing cytoprotection in mammals, especially humans, will generally range from about 0.1 mg/kg to about 100 mg/kg, preferably from about 1 mg/kg to about 100 mg/kg. The dosage may be administered in single or divided individual doses.

Any suitable route of administration may be employed for providing a mammal, especially a human with an effective dosage of a leukotriene antagonist. For example, oral, rectal, transdermal, parenteral, intramuscular, intravenous and the like may be employed. Dosage forms include tablets, troches, dispersions, suspensions, solutions, capsules and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, panoic, pantothenic, phosphoric, succinic, sulfuric, tataric acid, p-toluenesulfonic and the like. Particularly preferred are hydrobromic, hydrochloric, phosphoric and sulfuric acids.

The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use is from about 0.001 mg to about 10 mg (preferably from about 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from about 0.1 mg to about 100 mg (preferably from about 1 mg to about 100 mg and more preferably from about 10 mg to about 100 mg) of a compound of Formula I per kg of body weight per day.

For administration by inhalation, the compounds of the present invention are conveniently delivered in the form of an aerosol spray presentation from pressurized packs or a nebulise. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension | mg/ml |
|---|---|
| Compound of Formula I | 10 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 1 ml | |

| Tablet | mg/tablet |
|---|---|
| Compound of Formula I | 25 |
| Microcrystalline Cellulose | 325.0 |
| Providone | 14.0 |
| Microcrystalline Cellulose | 90.0 |
| Pregelatinized Starch | 43.5 |
| Magnesium Stearate | 2-2.5 |
| | 500 |

| Capsule | |
|---|---|
| Compound of Formula I | 25 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000. Combinations of a compound of the Formula I and other active ingredients will generally also be within the aforementioned range, but in each case, an effective dose of each active ingredient should be used.

NSAIDs can be characterized into five groups:
 (1) the propionic acid derivatives;
 (2) the acetic acid derivatives;
 (3) the fenamic acid derivatives;
 (4) the biphenylcarboxylic acid derivatives; and
 (5) the oxicams
or a pharmaceutically acceptable salt thereof. NSAIDs which are within the scope of this invention are those disclosed in EP No. 140,684.

Pharmaceutical compositions comprising the Formula I compounds may also contain inhibitors of the biosynthesis of the leukotrienes such as are disclosed in EP No. 138,481 (April 24, 1985), EP No. 115,394 (Aug. 8, 1984), EP No. 136,893 (Apr. 10, 1985), and EP No. 140,709 (May 5, 1985), which are hereby incorporated herein by reference.

The compounds of the Formula I may also be used in combination with leukotriene antagonists such as those disclosed in EP No. 106,565 (Apr. 25, 1984) and EP No. 104,885 (Apr. 4, 1984) which are hereby incorporated herein by reference and others known in the art such as those disclosed in European Patent Application Nos. 56,172 (July 21, 1982) and 61,800 (Oct. 6, 1982); and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application No. 11,067 (May 28, 1980) or thromboxane antagonists such as those disclosed in U.S. Pat No. 4,237,160. They may also contain histidine decarboxylase inhibitors such as α-fluoromethylhistidine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, aminothiadiazoles disclosed in EP No. 40,696 (Dec. 2, 1981) and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

Compounds of the present invention can be prepared according to the following methods.

METHOD A

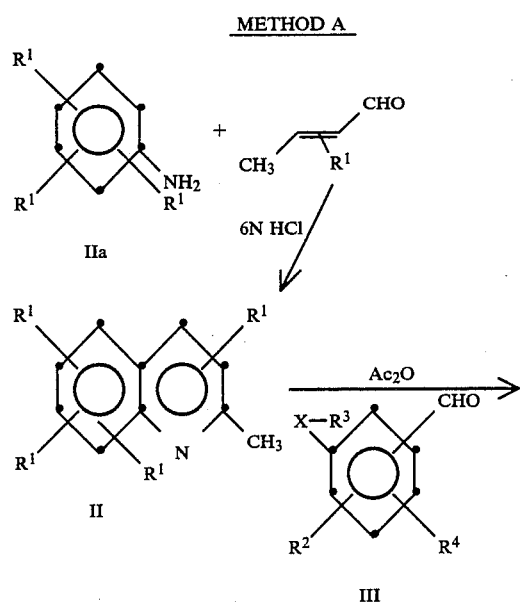

PREPARATION OF INTERMEDIATE III

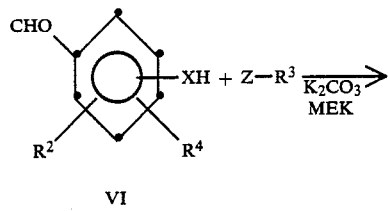

-continued

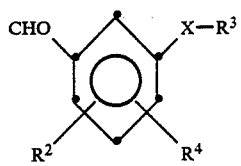

*When $R^3$ contains Q=$COOR^2$ and $R^2$ is not H, then the ester may be hydrolyzed with base to provide Q=COOH or a salt thereof.

Referring to Method A, an aniline derivative of Formula IIa is reacted by heating with crotonaldehyde and a strong mineral acid such as aqueous hydrochloric acid to provide the substituted quinaldine derivative of structure II. When IIa is unsymmetrical two regioisomers of II may be obtained. The products are purified by precipitation of the zinc chloride adducts or by standard chromatographic techniques. II is reacted with a benzaldehyde derivative of structure III by heating with a dehydrating agent, most preferably by heating with acetic anhydride to provide the 2-styrylquinoline derivatives of structure IV which are purified by removal of solvents and standard chromatographic purification. The 2-styrylquinoline esters (IV) may be hydrolyzed in a mixture of a polar solvent such as tetrahydrofuran (THF) and a strong aqueous base such as sodium hydroxide to provide the salts V, which generally precipitate from the reaction mixture and are collected by filtration.

The requisite aldehydes of structure III are prepared by reaction of the readily available benzaldehyde derivatives VI with an alkanoic acid ester or tetrazole terminally substituted with a good leaving group (Z) such as Br or I in the presence of an appropriately strong base such as $K_2CO_3$ for X=O, S, and NaH for —NHR, in an inert solvent (e.g., MEK, methyl ethyl ketone), with heating. III is purified by chromatography.

METHOD B

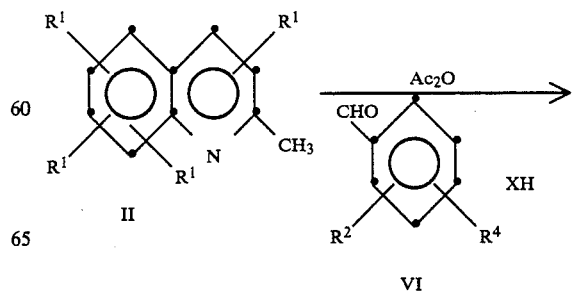

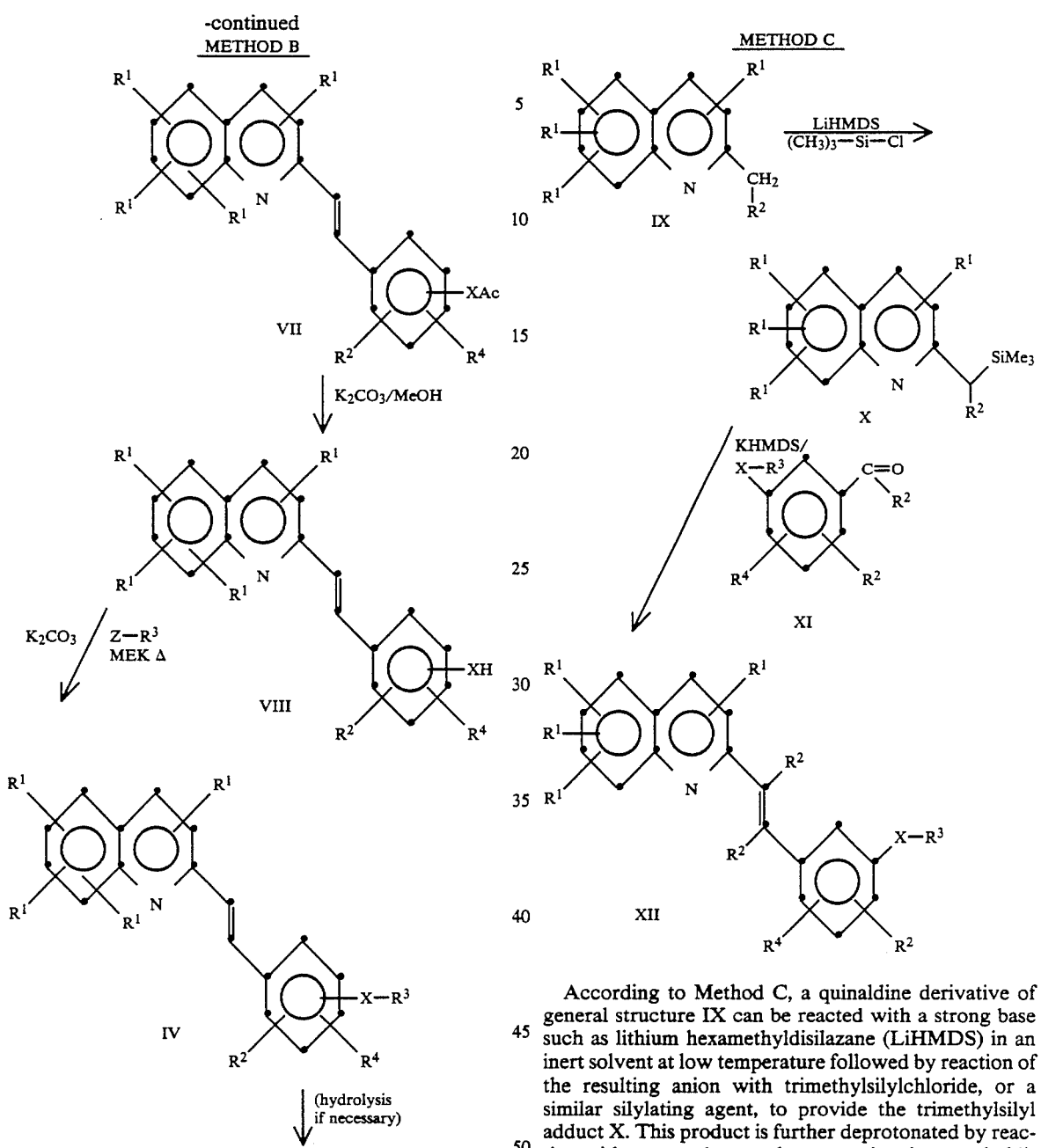

Alternatively (Method B), a quinaldine of structure II can be reacted with a benzaldehyde derivative of structure VI by heating with a dehydrating agent, preferably acetic anhydride, to provide the 2-styrylquinoline acetate of structure VII. The acetate is hydrolyzed by reaction with a suitably strong aqueous base such as $K_2CO_3$ (for X=O, S) or NaOH (for X=NR) in the presence of a solubilizing co-solvent such as methanol to give the products of structure VIII. VIII is reacted with an alkanoic acid ester nitrile or tetrazole, terminally substituted with a good leaving group (Z) such as Br or I in the presence of a suitably strong base such as $K_2CO_3$ (for X=O, S) or NaH (for X=NR) in an inert solvent such as MEK or THF with heating to provide the adducts IV.

According to Method C, a quinaldine derivative of general structure IX can be reacted with a strong base such as lithium hexamethyldisilazane (LiHMDS) in an inert solvent at low temperature followed by reaction of the resulting anion with trimethylsilylchloride, or a similar silylating agent, to provide the trimethylsilyl adduct X. This product is further deprotonated by reaction with a strong base such as potassium hexamethyldisilazane (KHMDS) at low temperature in an inert solvent such as THF. The resulting anion is reacted with an aldehyde or ketone of general structure XI at low temperature followed by warming to provide the 2-styrylquinoline adducts of general structure XII.

METHOD D

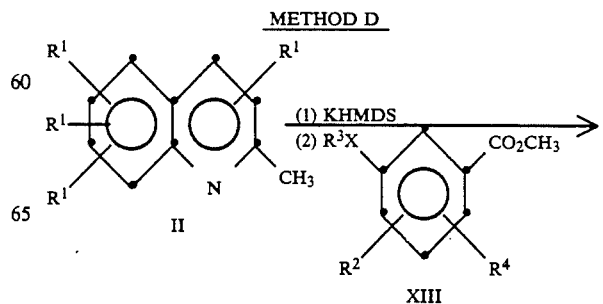

-continued
METHOD D

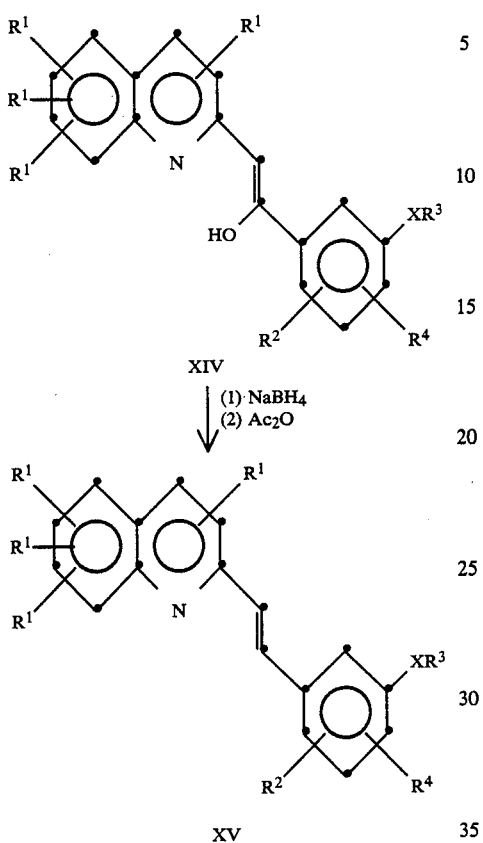

In Method D, a quinaldine derivative of general structure II is reacted with a strong base such as potassium hexamethyldisilazane or the like in an inert solvent such as THF at low temperature followed by reaction of the resulting anion with an ester of general structure XIII followed by warming and isolation of the adduct of general formula XIV by standard chromatographic techniques. XIV is reduced with a reducing agent such as NaBH$_4$ in a solvent such as methanol or ethanol followed by dehydration of the resulting intermediate alcohol with a dehydrating agent such as acetic anhydride to provide the 2-styrylquinoline adducts of general formula XV.

METHOD E - Ethers and Thioethers

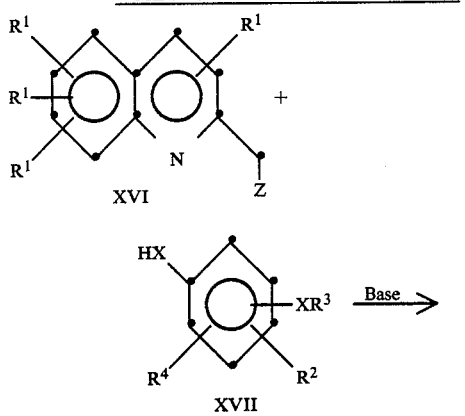

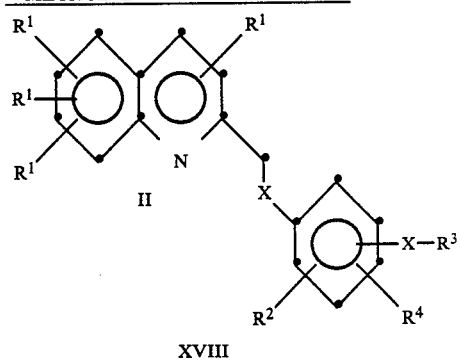

Z=halogen (preferably Cl, or Br or I) or a good leaving group such as —OSO$_2$—R' (e.g., tosylate or mesylate).

Referring to Method E, a quinaldine derivative of general structure XVI is prepared by standard methods from quinaldine derivatives of Formula II. XVI is then reacted with a compound of Formula XVIII in the presence of a suitable base such as NaOH, NaH, K$_2$CO$_3$ or NaOMe when HY=OH, SH, or NaH, etc. when HY=NHR in an inert solvent such as THF, dioxane, DMF, etc., with warming if necessary to provide the adducts XVIII.

METHOD F - Ethers and Thioethers

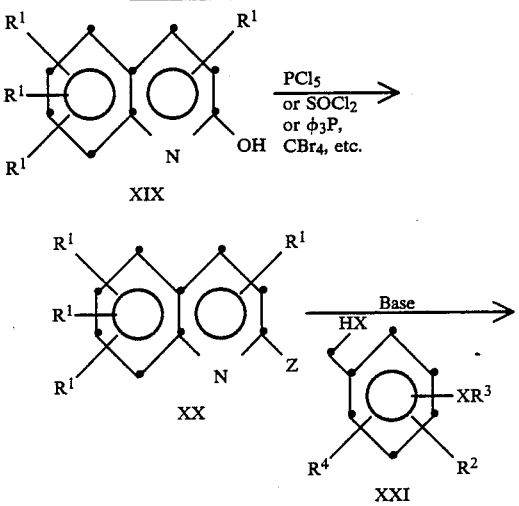

X=O, S, NHR$_2$

Alternatively, ethers and thioethers of Formula I may by prepared according to Method F. A 2-hydroxyquinoline of general structure XIX is reacted with a halogenating agent such as PCl$_5$, SOCl$_2$, SO$_2$Cl$_2$ or triphenylphosphine-carbon tetrabromide or the like to produce the 2-halogen-substituted quinolines of general structure XX. The halides XX are reacted with the anions derived from the compounds of general structure XXI (by reaction of XXI with a strong base such as NaH, KH, KHMDS etc.) in an inert solvent such as THF, dioxane, DMF etc., with heating in necessary to produce the adducts of general structure XXII.

METHOD G - Acetylenes

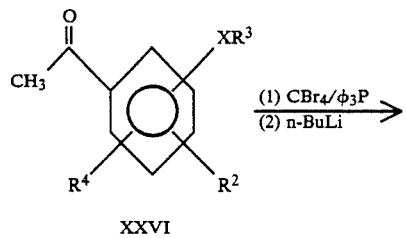

XXVI

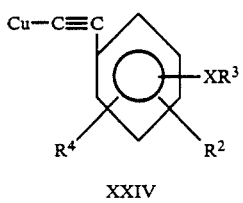

XXVII

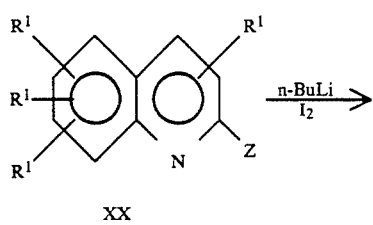

XXIV

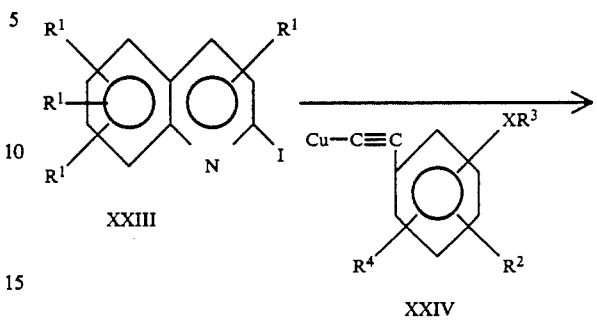

XXIII

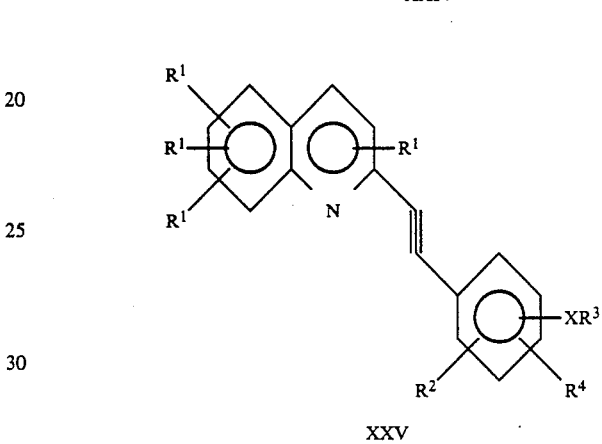

XXV

Referring to Method G, the required copper acetylides, XXIV, are prepared from the acetylides XXVII using known methods. The acetylides are prepared from the corresponding acetophenones XXVI by treatment with CBr$_4$/$\phi_3$P followed by treatment with n-BuLi.

A quinoline of structure XX (Method F) is transformed to quinoline XXIII using standard methods. The iodide XXIII is reacted with the copper acetylide of general structure XXIV in an inert solvent, such as pyridine, with heat to produce adducts of general structure XXV.

According to Method H, a styryl quinoline derivative of structure VII (Method B) is treated with bromine in an inert solvent, preferably acetic acid, with heating to provide vinyl bromo derivative XXVI. The vinyl bromo derivative is reacted with a suitable strong base such as 1,8-diazabicyclo[5.4.0]-undec-7-ene in an inert solvent such as THF to afford acetylene XXVII. Acetylene XXVII is transformed to quinoline XXVIII as described in Method B for vinyl quinoline VII.

METHOD H - Alternate Preparation of Acetylenes

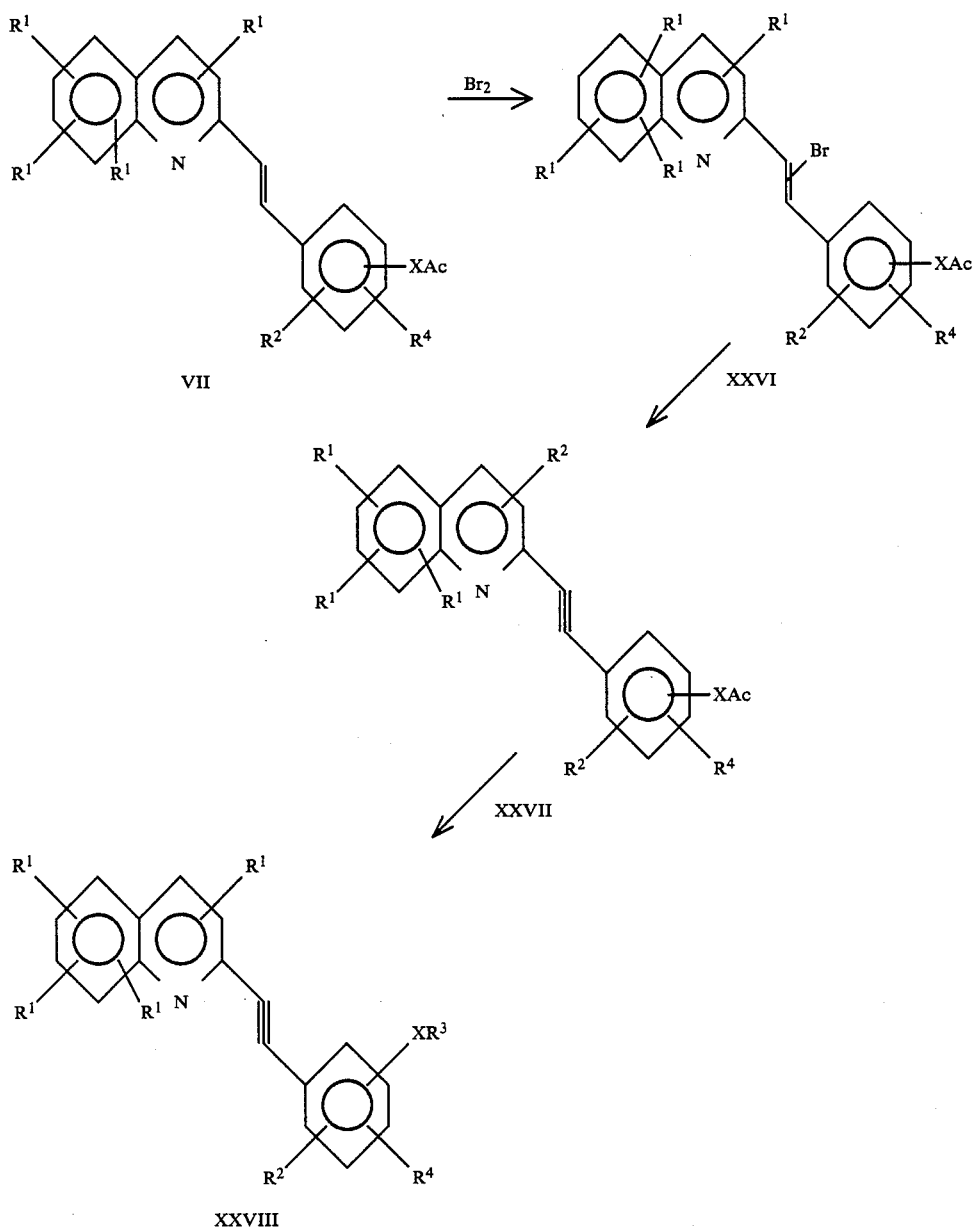

It will be understood by those skilled in the art that the selection of the most appropriate synthetic method will depend on the desired end product and the compatibility of the substituents with the reaction conditions. In the tables of examples that follow, an alphanumeric column is provided as a guide which refers, for each item, both to a general Method and to a detailed example for an analogous compound.

The following examples, which are representative of Formula I compounds, further define the invention and are provided as illustrative and not as limiting.

Temperatures are in degrees Celsius.

Compounds of Formula E were prepared as shown in Table 1.

TABLE 1

[Structure: substituted quinoline with R₁″ at top, R₁′ on benzo ring, connected via vinyl (CH=CH) at 2-position to a phenyl ring bearing X—R³ at 4′ and R‴ at 6′ position]

| EX # | $R_1'$ | $R_1''$ | R‴ | X—R³ | M.P. | Prep. |
|---|---|---|---|---|---|---|
| 1 | 5-Cl | H | H | —O(CH$_2$)$_3$—CO$_2$Et | 42–44 | A,5 |
| 2 | 6-Cl | H | H | —O(CH$_2$)$_3$—CO$_2$Et | 90–92 | A,5 |
| 3 | 7-Cl | H | H | —O(CH$_2$)$_3$—CO$_2$Et | 85–87 | A,5 |
| 4 | 6-Br | H | H | —O(CH$_2$)$_3$—CO$_2$Et | 95–96 | A,5 |
| 5 | 7-Br | H | H | —O(CH$_2$)$_3$—CO$_2$Et | 92–93 | A,5 |
| 6 | 7-F | H | H | —O(CH$_2$)$_3$—CO$_2$Et | 73–75 | A,5 |
| 7 | 6-F | H | H | —O(CH$_2$)$_3$—CO$_2$Et | 68–70 | A,5 |
| 8 | 5-CF$_3$ | H | H | —O(CH$_2$)$_3$—CO$_2$Et | 57–58 | A,5 |
| 9 | 7-CF$_3$ | H | H | —O(CH$_2$)$_3$—CO$_2$Et | 57–58 | A,5 |
| 10 | 6,7-diCl | H | H | —O(CH$_2$)$_3$—CO$_2$Et | 97–98 | A,5 |
| 11 | 6-CH$_3$ | H | H | —O(CH$_2$)$_3$—CO$_2$Et | 89–91 | A,5 |
| 12 | H | H | H | —OCH$_2$CO$_2$Me | 110–112 | B,12 |
| 13 | H | H | H | —SCH$_2$CO$_2$Me | (M$^+$m/e335)* | B,35 |
| 14 | H | H | 5′-OCH$_2$CO$_2$Me | —OCH$_2$CO$_2$Me | 82–83 | B,34 |
| 15 | 6-Br | H | H | —OCH$_2$CO$_2$CH$_3$ | 119–120 | A,5 |
| 16 | 6-F | H | H | —CH$_2$CO$_2$CH$_3$ | 97–98 | A,5 |
| 17 | 6-Cl | H | H | —OCH$_2$CO$_2$CH$_3$ | 105–107 | A,5 |
| 18 | 6-Me | H | H | —OCH$_2$CO$_2$CH$_3$ | 100–102 | A,5 |
| 19 | H | H | H | —OCH$_2$CO$_2$H | 185–187 | A,23 |
| 20 | H | H | H | —OCH$_2$CONMe$_2$ | 104–105.5 | A,20 |
| 22 | H | H | 5′propyl | —OCH$_2$CO$_2$CH$_3$ | (M$^+$m/e361)* | A,22 |
| 23 | H | H | 5′propyl | —OCH$_2$COOH | 97–98 | A,23 |
| 24 | H | H | H | —NHCOCOOEt | 123–125 | B,24 |
| 25 | 6-CH$_3$ | H | H | —OCH$_2$CONMe$_2$ | 149–151 | A,20 |
| 26 | 6-Cl | H | H | —OCH$_2$CONMe$_2$ | 151–153 | A,20 |
| 27 | 7-Br | H | H | —OCH$_2$CO$_2$CH$_3$ | 147–148 | A,5 |
| 28 | 7-Br | H | H | —OCH$_2$CO$_2$H | 245–247 | A,23 |
| 29 | 7-S-butyl | H | H | —OCH$_2$CO$_2$CH$_3$ | 56–57 | A,12 |
| 30 | H | propyl | H | —O(CH$_2$)$_3$COOH | 162–164 | A,23 |
| 31 | 6-(1-hexenyl) | H | H | —OCH$_2$CO$_2$CH$_3$ | 82–85 | A,31 |
| 32 | H | H | H | —O(CH$_2$)$_3$—CO$_2$H | 152–155 | A,23 |
| 33 | 8-butyl | H | H | —O(CH$_2$)$_3$—CO$_2$Et | (M$^+$m/e375)* | A,5 |
| 34 | H | H | 5′-O—(CH$_2$)$_3$—COOH | —O(CH$_2$)$_3$—COOH | 188–190 | B,34 |
| 35 | 7-Br | H | H | —S—(CH$_2$)$_3$—COOEt | 87–88 | B,35 |
| 36 | 7-Br | H | H | —S—(CH$_2$)$_3$—CO$_2$Na | 275–278(d) | B,36 |
| 37 | 7-Br | H | H | —SO$_2$—(CH$_2$)$_3$—CO$_2$Et | 109–110 | B,37 |
| 38 | 7-Br | H | H | —SO$_2$—(CH$_2$)$_3$—CO$_2$Na | 215–218(d) | B,38 |
| 39 | 7-Br | H | 6′-Cl | —O—(CH$_2$)$_3$—CO$_2$Na | 215–220 | B,39 |
| 54 | 7-Br | H | H | —O—CH(CH$_3$)CO$_2$Me | 101–102° | B,54 |
| 55 | 7-Br | H | H | —O—CH(CH$_3$)CO$_2$H | | B,55 |
| 56 | 7-Br | H | H | —O—CH$_2$—CH(CH$_3$)<br>              \|<br>            CH$_2$CO$_2$Et | | A,56 |
| 57 | 7-Br | H | H | —O—CH$_2$—CH(CH$_3$)<br>              \|<br>            CH$_2$CO$_2$Na | 197–203° | A,57 |
| 58 | 7-Br | H | H | —O—(CH$_2$)$_3$—C≡N | | B,12 |
| 59 | 7-Br | H | H | —O—(CH$_2$)$_3$-tetrazole** | | B,59 |
| 60 | 7-Br | H | H | —O—(CH$_2$)$_2$—C—(CH$_3$)$_2$<br>                   \|<br>                 CH$_2$CO$_2$Me | 50–52° | B,60 |
| 61 | 7-Br | H | H | —O—(CH$_2$)$_2$—C—(CH$_3$)$_2$<br>                   \|<br>                 CH$_2$CO$_2$Na | | B,61 |

TABLE 1-continued

E

| EX # | $R_1'$ | $R_1''$ | $R'''$ | $X-R^3$ | M.P. | Prep. |
|------|--------|---------|--------|---------|------|-------|
| 62 | 6,7 di-Cl | H | H | $-O-C(CH_3)-CO_2H$ | 181°(d) | B,55 |
| 63 | 7-$CF_3$ | H | H | $-O-C(CH_3)-CO_2H$ | 211°(d) | B,55 |
| 64 | 7-Br | H | H | $-O-CH_2$-tetrazole | 193(d) | B,71 |
| 65 | 7-Br | H | H | $-O-CH(CH_2CH_3)-CO_2Na$ | 219(d) | B,55 |
| 66 | 7-F | H | H | $-O-CH(CH_3)-CO_2Na$ | 235° | B,55 |
| 67 | 7-Cl | H | H | $-O-CH(CH_3)-CO_2H$ | 90–95° | B,55 |
| 68 | 7-Br | H | H | $-O-CH_2$-(phenyl)-$CO_2Me$ (meta) | 115–117° | B,55 |
| 69 | 7-Br | H | H | $-O-CH_2$-(phenyl)-$CO_2Me$ (para) | 160–161° | B,55 |
| 70 | 7-Br | H | H | $-O-CH(CH_3)$-tetrazole | 207°(d) | B,71 |
| 71 | 7-Cl | H | H | (+,−)-$O-CH(CH_3)$-tetrazole | 100–103° | B,71 |
| 72 | 7-Cl | H | H | (+)-$O-CH(CH_3)-COOH$ | 102–104° | 72 |
| 73 | 7-Cl | H | H | (−)-$O-CH(CH_3)-COOH$ | 103–105° | 73 |
| 74 | 7-Cl | H | H | (−)-$O-CH(CH_3)-CONH_2$ | 195–197° | 74 |
| 75 | 7-Cl | H | H | (+)-$O-CH(CH_3)-CONH_2$ | 195–197° | 75 |

TABLE 1-continued

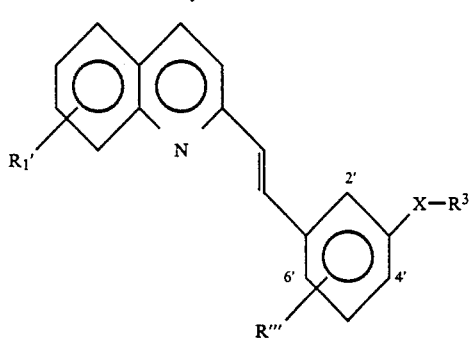

| EX # | $R_1'$ | $R_1''$ | $R'''$ | $X-R^3$ | M.P. | Prep. |
|---|---|---|---|---|---|---|
| 76 | 7-Cl | H | H | (+)-O—CH(CH$_3$)—CN | 147–148* | 76 |
| 77 | 7-Cl | H | H | (−)-O—CH(CH$_3$)—CN | 147–148* | 77 |
| 78 | 7-Cl | H | H | (+)-O—CH(CH$_3$)-tetrazole | 149–151 | 78 |
| 79 | 7-Cl | H | H | (−)-O—CH(CH$_3$)-tetrazole | 148–150 | 79 |

(d) = decomposed
*molecular ion
**tetrazole = 1H (or 2H)-5 tetrazolyl moiety

Compounds of Formula F were prepared as shown in Table 2.

TABLE 2

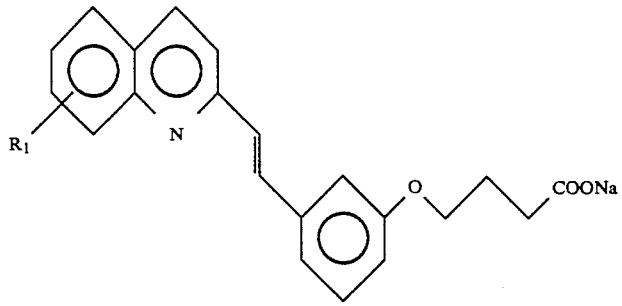

| | | | Analysis | | | | | | | | |
|---|---|---|---|---|---|---|---|---|---|---|---|
| | | | Calcd. | | | | Found | | | | |
| EX # | $R_1$ | EMP. FORM. | C | H | N | Hal | Na | C | H | N | Hal | Na | Prep. |
| 41 | 5-Cl | m.p. 232–237 | | | | | | | | | | |
| 42 | 6-Cl | $C_{21}H_{17}ClNO_3Na \cdot \frac{1}{2}H_2O$ | 63.24 | 4.55 | 3.51 | 8.89 | 5.77 | 63.64 | 4.59 | 3.49 | 8.60 | 5.73 | A,45 |
| 43 | 7-Cl | $C_{21}H_{17}ClNO_3Na \cdot \frac{1}{2}H_2O$ | 63.24 | 4.55 | 3.51 | 8.89 | 5.77 | 63.88 | 4.61 | 3.56 | 8.93 | 5.56 | A,45 |
| 44 | 6-Br | $C_{21}H_{17}BrNO_3Na$ | 58.08 | 3.95 | 3.23 | 18.40 | | 57.58 | 4.02 | 3.28 | 18.76 | | A,45 |
| 45 | 7-Br | $C_{21}H_{17}BrNO_3Na$ | 58.08 | 3.95 | 3.23 | 18.40 | | 57.91 | 4.08 | 3.18 | 18.33 | | A,45 |
| 46 | 7-CF$_3$ | $C_{22}H_{17}F_3NO_3Na \cdot \frac{1}{2}H_2O$ | 61.18 | 4.20 | 3.24 | 13.18 | | 61.24 | 4.30 | 3.12 | 12.90 | | A,45 |
| 47 | 5-CF$_3$ | $C_{22}H_{17}F_3NO_3Na \cdot \frac{1}{2}H_2O$ | 61.18 | 4.20 | 3.24 | 13.18 | | 61.28 | 4.41 | 3.16 | 12.62 | | A,45 |
| 48 | 7-F | m.p. 240–245 | | | | | | | | | | |
| 49 | 6,7-diCl | $C_{21}H_{16}Cl_2NO_3Na \cdot \frac{1}{2}H_2O$ | 58.21 | 3.92 | 3.23 | 16.56 | 5.10 | 58.10 | 3.99 | 3.41 | 16.58 | 5.10 | A,45 |
| 50 | 5,6-diCl | m.p. 255–260° | | | | | | | | | | |
| 51 | 6-Me | $C_{22}H_{20}NO_3Na \cdot \frac{1}{2}H_2O$ | 69.82 | 5.59 | 3.70 | — | 6.08 | 69.90 | 5.52 | 3.77 | — | 6.11 | A,45 |
| 53 | 6-F | $C_{21}H_{17}FNO_3Na$ | 67.50 | 4.59 | 3.75 | 5.09 | 6.15 | 66.86 | 4.80 | 3.59 | 4.91 | 6.41 | A,45 |

Compounds of Formula G were prepared as shown in Table 3.

| 21 | NHCOCOOEt | 160–162 | B,21 |
| 64 | OCH$_2$CO$_2$Me | 130–132 | A,5 |

EXAMPLE 5

Ethyl 4-(3-(2-(7-bromoquinolin-2-yl)ethenyl)phenoxy)butyrate

Step 1. Preparation of ethyl 4-(3-formylphenoxy)butanoate

A solution of ethyl 4-iodo-butyrate (100 g) and m-hydroxybenzaldehyde (42 g) in methyl ethyl ketone (500 ml) in the presence of potassium carbonate (142 g) was refluxed overnight. The reaction mixture was cooled diluted with dichloromethane filtered and evaporated. Distillation afforded the title compound; b.p. 140–150° C. (0.4 mm).

Step 2. Preparation of ethyl 4-(3-(2-(7-bromoquinolin-2-yl)ethenyl)phenoxy)butyrate A solution of 7-bromoquinaldine (22 g, 0.1M) and ethyl 4-(3-formylphenoxy)butanoate (20 g) in acetic anhydride (100 ml) was heated at 135° for 34 hours cooled and evaporated. Flash chromatography of the residue using 1:1 ether in hexane as eluant afforded crude adduct. Recrystallization from hexane ethyl acetate afforded the title compound: m.p. 92–93°.

EXAMPLE 12

Methyl 2-(3-(2-(Quinolin-2-yl)ethenyl)phenoxy)acetate

Step 1. Preparation of 2-(2-(3-acetoxyphenyl)ethenyl)quinoline

A solution of 3-hydroxybenzaldehyde (25 g) and quinaldine (28 ml) in acetic anhydride (150 ml) was heated overnight at 130° cooled and evaporated in vacuo. Purification of the residue by flash chromatography using 35% ether in hexane to 45% ether in hexane afforded the title quinoline compound after recrystallization from ether/hexane, m.p. 86–87°.

Step 2. Preparation of 2-(2-(3-hydroxyphenyl)ethenyl)quinoline

To a solution of the acetate (5 g) in methanol 250 ml was added sodium carbonate (500 mg). The suspension was stirred at room temperature for 2 days. pH 7 buffer (25% NH$_4$OAc) was added and the precipitated solid was filtered off. The solid was triturated in ethanol, filtered and dried in vacuo to give the title quinoline compound: m.p. 210–212°.

Step 3.

A suspension of milled potassium carbonate (0.5 g), quinoline from Step 2 (1.1 g), and methylbromoacetate (4.0 ml) in acetone (25 ml) were refluxed overnight. The reaction mixture is poured onto water, extracted with ethyl acetate dried and evaporated. Chromatography of the residue on SiO$_2$ using 30 to 40% ether/hexane afforded the title compound: m.p. 110–112°.

EXAMPLE 20

2-(3-(2-(Quinolin-2-yl)ethenyl)phenoxy)acetic acid dimethylamide

A solution of the ester Example 12 (0.6 g) was heated overnight at 60° in THF (25 ml) saturated with dimethylamine in a pressure bottle. The reaction mixture was evaporated under vacuo. Flash chromatography of the residue using 50% to 80% ethyl acetate in hexane afforded the title compound: m.p. 104–105.5°.

EXAMPLE 21

4-[2-(Quinolin-2-yl)ethenyl]-N-[1,2-dioxo-2-ethoxyethyl]aniline

Step 1. Preparation of 4-[2-(quinolin-2-yl)ethenyl]N,N-diacetylaniline

A mixture of quinaldine (10 ml) and 4-acetamidobenzaldehyde (12 g) in acetic anhydride (60 ml) was stirred at 130° C. for 2 days, then cooled to room temperature, evaporated to dryness and chromatographed on column of flash silica gel (800 g) using as solvent a mixture of hexane-ethyl acetate (1:1) to provide the title product as a yellow solid: m.p. 148–150° C.

Step 2. Preparation of 4-[2-(quinolin-2-yl)ethenyl]aniline

A suspension of diacetate (6 g) in MeOH (100 ml) was warmed until homogeneous solution was obtained and then 5N NaOH (36 ml) was added and the mixture was refluxed overnight. The mixture was cooled to 0° C. and poured into aqueous pH 7 buffer (25% ammonium acetate in water) and the solid was filtered and rinsed with H$_2$O. The solid was chromatographed on column of flash silica gel (500 g) using toluene-ethyl acetate (5:1) as eluant to give a solid which was recrystallized from ethyl acetate (50 ml) to provide the title product as an orange solid: m.p. 178–180° C.

Anal. Calcd for C$_{17}$H$_{14}$N$_2$:

Calc.: C, 82.89; H, 5.73; N, 11.38

Found: C, 83.13; H, 5.93; N, 11.29.

Step 3.

To a solution of amine (492 mg) in THF (15 ml) was slowly added ethyl oxalyl chloride (0.34 ml) and stirred at room temperature for 15 minutes. Then the reaction mixture was poured into aqueous pH 7 buffer (30 ml) and the formed solid was filtered to be purified on column of flash silica gel (150 g) using a mixture of dichloromethane-acetone (10:0.3) as eluant to provide the title product as a white solid: m.p. 160–162° C.

EXAMPLE 22

Methyl 2-(3-(2-(quinolin-2-yl)ethenyl)-5-propylohenoxy)acetate

Step 1. Preparation of 5-methoxyisophthalic acid dimethyl ester

KMnO$_4$ (380 g) was added in portions to a hot and vigorously stirred solution of dimethyl anisole. Portions were added at such a rate to keep the mixture boiling gently. The reaction mixture was refluxed a further hour and then ethanol (100 ml) was added to destroy remaining KMnO$_4$. The t-BuOH was distilled. The residue was filtered and washed with water. The filtrate was acidified (to pH 3.5) and the di-acid was filtered and dried. To a solution of di-acid in methanol (1 L) was added sulfuric acid (6 ml). The mixture was refluxed for 7 days. Upon cooling to about 5°, the product crystallized. The white solid was filtered, washed with cold methanol and dried under vacuo: m.p. 108–109°.

Step 2. Preparation of bis-(5-methoxy-1,3-phenylene)methanol

To a solution of dimethyl ester (10 g) in tetrahydrofuran (300 ml) at 0° was added LiAlH₄ (6 g) in three portions over 30 minutes. The reaction mixture is stirred overnight at room temperature. Water (6 ml) was then slowly added, followed by NaOH (2N, 6 ml) and water (9 ml). After stirring 1 hour at room temperature the aluminum salts were filtered off. The filtrate was evaporated in vacuo and co-evaporated with toluene to afford the title compound which was used as such for the next step.

Step 3. Preparation of 5-methoxyisophthaldehyde

To a solution of the diol (6.8 g) in ethyl acetate (300 ml) was added 40 g of $MnO_2$ in 3 portions over 3 days. The reaction was filtered and evaporated. Recrystallization of the residue from ether/hexane afforded the title compound: m.p. 112–113.

Step 4. Preparation of 3-methoxy-5-(1-propenyl)-benzaldehyde

To a suspension of ethyltriphenyphosphonium iodide (10 g) in THF (150 ml) at 0° was added dropwise n-butyllithium (15 ml of 1.5M in hexane). The reaction mixture was stirred 1 hour at 0° and cooled to −30°. The reaction mixture at −30° was added dropwise to a solution of 5 methoxyisophthaldehyde (3.2 g) in THF (150 ml) at −30° and allowed to warm up to room temperature. After 2 hours at room temperature the reaction mixture was quenched with NH₄OAc buffer (100 ml). The reaction mixture was extracted with ethyl acetate, dried and evaporated. Flash chromatography of the residue using 15% ethyl acetate hexane afforded the title compound as a mixture of cis and trans isomers.

PMR (CDCl₃), 1.9 (m, 3H), 3.85 (d, 3H), 5.8–6.0 (m, 1H), 6.3–6.5 (m,1H), 7.1 (m, 1H), 7.2–7.3 (m, 1H), 7.35–7.45 (m, 1H), 7.95 ppm (d, 1H).

Step 5. Preparation of 3-methoxy-5-propyl-benzaldehyde

A mixture of 3-methoxy-5-(1-propenyl)benzaldehyde (1.6 g) and platinum oxide (150 mg) in ethyl acetate (150 ml) were hydrogenated at 16 psi in a Parr hydrogenator for 5 hours. The mixture was filtered through a celite/charcoal plug and evaporated. Purification of the residue by flash chromatography using 12% ethyl acetate in hexane afforded the title compound.

PMR (CDCl₃): 0.95 (t, 3H), 1.65 (m, 2H), 2.65 (t, 2H), 3.85 (s, 3H), 7.0 (m, 1H), 7.22 (m, 1H), 7.30 (m, 1H), 9.85 ppm (s, 1H).

Step 6. Preparation of 3-hydroxy-5-propyl-benzaldehyde

To a solution of sodium hydride (183 mg) and ethanethiol (0.6 ml) in DMF (15 ml) was added dropwise a solution of 3-methoxy-5-propyl-benzaldehyde (0.9 g). The reaction mixture was heated for 3 hours at 150°, quenched with NH₄OAc buffer and extracted with ethyl ether. The ethyl ether layer was dried (Na₂SO₄) and evaporated. Flash chromatography of the residue using 30% ether in hexane afforded the title compound.

PMR (CDCl₃): 0.90 (t, 3H), 1.65 (m, 2H), 2.6 (t, 2H), 5.35 (s, 1H), 6.9 (m, 1H), 7.17 (m, 1H), 7.28 (m, 1H), 9.90 ppm (s, 1H).

Step 7. Preparation of Methyl 2-(3-formyl-5-propylphenoxy)acetate

A mixture of 3-hydroxy-5-propyl-benzaldehyde potassium carbonate (0.7 g) and methyl bromoacetate (0.8 ml) in methyl ethyl ketone (6 ml) were heated at 70° for 4 hours. The reaction was filtered and evaporated. Flash chromatography of the residue using 30% ether in hexane afforded the title compound.

PMR (CDCl₃): 0.95 (t, 3H), 1.70 (m, 2H), 2.65 (t, 2H), 3.85 (s, 3H), 4.70 (s, 2H), 7.05 (m, 1H), 7.18 (m, 1H), 7.35 (m, 1H), 9.8 ppm (s, 1H).

Step 8.

A solution of the aldehyde (0.4 g), quinaldine (0.23 ml) and acetic anhydride were heated at 125° C. for 65 hours. The reaction mixture was evaporated under vacuo. Flash chromatography of the residue using 25 to 30% ether in hexane afforded the title compound as an oil.

Mass spectra showed a molecular ion at m/e 361.

PMR (CDCl₃): 0.95 (t, 3H), 1.6 (m, 2H), 2.6 (t, 3H), 3.8 (s, 3H), 4.7 (s, 2H), 6.75 (m, 1H), 7.0 (m, 1H), 7.0–7.8 (m, 7H), 8.05 (d, 1H), 8.15 ppm (d, 1H).

EXAMPLE 23

2-(3-(2-(Quinolin-2-yl)ethenyl)-5-propyl-phenoxy)acetic acid

A solution of the methyl ester (Example 23) (0.25 g) in THF (7 ml), MeOH (3 ml) and 1N NaOH (2.6 ml) was stirred 3 hours at room temperature. The reaction was diluted with distilled water (50 ml) and acidified with vigorous stirring to pH 3 using 2N HCl. The yellow precipitate was filtered and dried under high vacuum to yield the title compound: m.p. 97–98°.

Anal. Calcd for $C_{22}H_{21}NO_3$:
Calc.: C, 76.06; H, 6.09; N, 4.03
Found: C, 75.77; H, 6.07; N, 3.93.

EXAMPLE 24

3-[2-(Quinolin-2-yl)ethenyl]-N-ethyl oxalyl aniline

Step 1. Preparation of 3-[2-(quinolin-2-yl)ethenyl]nitrobenzene

A mixture of quinaldine (8 g) and m-nitrobenzaldehyde (8.4 g) in acetic anhydride (24 ml) was stirred at 130° C. overnight. The mixture was cooled to room temperature and poured into aqueous pH 7 buffer (250 ml). The solid was chromatographed on column of flash silica gel using as eluant dichloromethane to afford a solid which was recrystallized from ethyl acetate to afford the title product as a yellow solid: m.p. 145–147° C.

Anal. Calcd for $C_{17}H_{12}N_2O_2$:
Calc.: C, 790; H, 4.38; N, 10.14 Found: C, 74.15; H, 4.70; N, 10.10.

Step 2. Preparation of 3-[2-(quinolin-2-yl)ethenyl]aniline

To a warm solution of nitro (5 g) in EtOH (70 ml) and acetic acid (70 ml) was added powdered iron (4 g) and refluxed (120° C.) for 30 minutes. The reaction mixture was cooled to 0° C. and poured into aqueous pH 7 buffer (500 ml). The solid was filtered rinsed with H₂O and chromatographed on column of flash silica gel (300 g) using toluene-ethyl acetate (5:2) as eluant to give a solid (3.6 g) which was recrystallized from hexane-ethyl acetate to afford the title product as a yellow solid: m.p. 158–160° C. Anal. Calcd for C Calc.: C, 82.89; H, 5.73; N, 11.38 Found: C, 82.54; H, 5.92; N, 11.27. P/1191A - 46 - 17255IA Step 3.

Using the same procedure as in Example 21, Step 3, but replacing the 4-[2-(quinolin-2-yl)ethenyl]aniline by 3-[2-(quinolin-2-yl)ethenyl]aniline afforded the title product: m.p. 123–125° C.

Anal. Calcd for $C_{21}H_{18}N_2O_3$: Calc.: C, 72.82; H, 5.24; N, 8.09 Found: C, 72.78; H, 5.55; N, 8.07.

EXAMPLE 31

Methyl 2-[3-
2-[6-(1-Hex-1(E,Z)-enyl)quinolin-2-yl]ethenyl-
phenoxy]acetate

Step 1. Preparation of 6-carbomethoxy-2-methyl quinoline

To a solution of 6-carboxy-2-methyl quinoline in MeOH (600 ml) was added concentrated $H_2SO_4$ and stirred for 3 days at room temperature. The reaction mixture was evaporated and the residue was diluted with $H_2O$ (250 ml) and ethyl acetate (250 ml), and transferred to a separatory funnel. A solution of saturated sodium bicarbonate in water (1 L) was added and extraction with ethyl acetate afforded a purple solid which was chromatographed on column of flash silica gel using hexane-ethyl acetate (2:1) as eluant to provide the title compound as a yellow solid: m.p. 98–101° C.

Step 2. Preparation of 6-hydroxymethyl-2-methyl quinoline

A solution of ester (4 g) in anhydrous THF (100 ml) was cooled to 0° C. and lithium aluminium hydride (1.5 g) was added portionwise over 30 minutes. After complete addition at 0° C., $H_2O$ (1.5 ml) was added carefully, then 2N NaOH (3 ml) and again $H_2O$ (3 ml). The mixture was stirred at room temperature for 30 minutes, filtered, rinsed with THF to give after evaporation the title product as a yellow solid: m.p. 134°–136° C.

Step 3. Preparation of 6-formyl-2-methyl quinoline

To a solution of alcohol (3 g) in ethyl acetate (100 ml) was added, by portion each 15 minutes. Four portions of 3.8 g of manganese (IV) oxide and stirred at room temperature for 1 hour after last addition. The reaction mixture was filtered on bed of celite, rinsed with ethyl acetate and the filtrate was evaporated to give the title product as a yellow solid: m.p. 102–104° C.

Step 4. Preparation of 6-(1-hex(E,Z)-enyl)-2-methyl quinoline

A suspension of n-pentyltriphenylphosphonium bromide (3.6 g) in anhydrous THF (30 ml) was cooled to 0° C. and 1.5M in n-BuLi in hexane (5.9 ml) was added slowly, stirred at 0° C. for 20 minutes then cooled to −78° C. A solution of aldehyde (1.0 g) in THF (5 ml) was added dropwise, stirred at −78° C. for 30 minutes, then 1 hour at room temperature. The reaction mixture was transferred to a separatory layer was extracted with ethyl acetate. The organic layers were washed with $H_2O$, dried over $Na_2SO_4$ and evaporated to give a residue which was purified on column of flash silica gel using hexane-ethyl acetate (5:1) as eluant to provide three fractions of desired product as its pure isomer (E isomer and Z isomer) and as a mixture Z/E (2:1).

PMR (CDCl$_3$) of isomer E 0.95 (t, 3H), 1.3–1.6 (m, 4H), 2.20–2.35 (m, 2H), 2.73 (s, 3H), 6.3–6.42 (m, 1H), 6.55 (d, 1H), 7.25 (d, 1H), 7.58 (s, 1H), 7.78 (dd, 1H), 7.9–8.0 (3 peaks, 2H).

PMR (CDCl$_3$) of isomer Z 0.9 (t, 3H), 1.3–1.55 (m, 4H), 2.35–2.50 (m, 2H), 2.73 (s, 3H), 5.72–5.85 (m, 1H), 6.55 (d, 1H), 7.28 (d, 1H), 7.58–7.68 (m, 2H), 7.95–8.02 (3 peaks, 2H).

Step 5

A solution of quinoline (Z/E (2:1)) (234 mg) and 3-carbomethoxymethyloxy benzaldehyde (200 mg) in acetic anhydride (2 ml) was stirred at 130° C. for 3 days. The reaction mixture was cooled to room temperature and evaporated to dryness and chromatographed on column of flash silica gel using a mixture of toluene-ethyl acetate (10:0.5) as eluant to provide an oil which was repurified as above but using hexane-ethyl acetate (5:1) as eluant to afford a pure sample of the title product as a yellow solid: m.p. 82–85° C.

Anal. Calcd for $C_{26}H_{27}NO_3$: Calc.: C, 77.78; H, 6.78; N, 3.49 Found: C, 77.78; H, 6.90; N, 3.40.

EXAMPLE 34

Bis-4,4-[5- 2-(Quinolin-2-yl)ethenyl
-1,3-phenylene]oxybutanoic acid

Step 1. Preparation of 2-(2-(3,5-dimethoxyphenyl)-5 ethenyl)-quinoline

A solution of 3,5-dimethoxybenzaldehyde (2.8 g), quinaldine (2.3 g) were heated overnight at 130° in acetic anhydride. The reaction mixture was cooled to room temperature and evaporated. Flash chromatography of the residue using 30% ether in hexane afforded the title compound 4 g as an oil which was used as such for the next step.

Step 2. Preparation of 2-(2-(3,5-dihydroxyphenyl)-ethenyl)-quinoline

The dimethyl ether was treated with BBr$_3$ as described in Example 39, Step 6 to give the title compound which was used as such in the next step. Step 3. Preparation of diethyl bis-4,4'-[5-(2-(quinolin-2-yl)ethenyl)-1,3-phenylene]-oxybutyrate A solution of the phenol (1 g), $K_2CO_3$ (1 g) and ethyl-4-iodobutyrate (2 g) in methylethylketone (30 ml) were refluxed overnight Flash chromatography of the residue using 70% ether in hexane afforded the title compound, which was used as such for the next step.

To the diester (0.3 g) in THF (2 ml) and EtOH (1.5 ml) was added 2N NaOH. The reaction mixture was stirred overnight at room temperature. The solution was evaporated under vacuo and redissolved in $H_2O$ (5 ml). HCl (2N) was added dropwise to pH 3. The deep yellow precipitate was filtered, washed with EtOH and dried under high vacuo.

PMR (CD$_3$SOCD$_3$) 2.0 (m, 4H), 2.4 (t, 4H), 4.0 (t, 4H), 6.5 (m, 1H), 6.9 (m, 2H), 7.5–8.0 (m, 6H), 8.35 ppm (d, 1H).

EXAMPLE 35

Ethyl 4-(3-(2-(7-Bromoquinolin-2-yl)ethenyl)thiophenoxy)butyrate

Step 1. Preparation of 7-bromo-2-(2-(3-acetoxy-)phenyl)ethenyl)quinoline

7-Bromoquinaldine (8.8 g) and m-hydroxybenzaldehyde (4.8 g) in acetic anhydride (50 ml) were heated at 130° two days. To the reaction mixture was added 50% ether in hexane (50 ml). The product was filtered and recrystallized from ethyl acetate/hexane: m.p. 138°–139°.

Step 2. Preparation of 7-bromo-2-(2-(3-hydroxyphenyl)ethenyl)quinoline

To a solution of the previous acetate (5 g) in methanol (300 ml) and tetrahydrofuran (100 ml) was added potassium carbonate (2 g). The reaction mixture was stirred 4 hours and then a solution (200 ml) of NH$_4$OAc (25%) in water was added. The 191°–193°.

Step 3. Preparation of 7-bromo-2-(2-(3-dimethylthio-carbamoyloxyphenyl)ethenyl)quinoline To phenol (4.5 g) in DMF (50 ml) was added sodium hydride (420 mg). The mixture was stirred for hour at 50°. To the resulting solution was added dimethylthiocarbamoyl chloride (2.0 g). After heating for 3 hours at 80°, the reaction mixture was poured into water (200 ml) and extracted with ethyl acetate. The organic layer was dried (Na$_2$SO$_4$) and evaporated. Chromatography of the residue using 30% ethyl acetate in hexane afforded the title compound.

PMR 1 (CDCl$_3$) 2.30 (s, 3H), 2.35 (s, 3H), 7.1 (m, 1H), 7.3–7.9 (m, 8H), 8.15 (d, 1H), 8.30 ppm (d, 1H).

Step 4. Preparation of 7-bromo-2-(2-(3-dimethyl-carbamylthiophenyl)ethenyl)quinoline The carbamate (4.5 g) was heated for 4 hours at 240° under N$_2$. Chromatography using 2% ethyl acetate in chloroform afforded the title compound which was used as is for the next step.

To thiocarbamate (2 g) in THF (50 ml) was added NaOMe (200 mg Na in 15 ml dry MeOH). The reaction was stirred 1 hour at 60°. Ethyl 4-iodo-butyrate (2 g) was added and the mixture was heated 2 hours at 60°. The reaction mixture was poured onto pH 7 buffer (200 ml of 25% aqueous NH$_4$OAc), extracted with ethyl acetate, dried and evaporated. Flash chromatography of the residue using 30% ether in hexane afforded the title compound: m.p. 87°–88°.

EXAMPLE 36

4-(3-(2-(7-Bromoquinolin-2-yl)ethenyl)thiophenoxy)-butyric acid sodium salt

To the ethyl ester of Example 35 (0.5 g) in ethanol (10 ml) and THF (3 ml) was added 2N sodium hydroxide. After stirring overnight at room temperature, the product was filtered. Trituration of the white solid with ethanol afforded the title compound: m.p. 275°–280° (d).

EXAMPLE 37

Ethyl 4-(3-(2-(7-Bromoquinolin-2-yl)ethenyl)phenyl-sulfonyl)butyrate

To the ethyl ester of Example 35 (0.9 g) in CH$_2$Cl$_2$ (25 ml) at 0° was added m-chloroperbenzoic acid (1 g). After stirring 1 hour at 0° calcium hydroxide (1 g) was added. The mixture was stirred 1 hour at room temperature. Flash chromatography of the residue using 50% ethyl acetate in hexane afforded the title sulfone: m.p. 109°–110°.

EXAMPLE 38

4-(3-(2-(7-Bromoquinolin-2-yl)ethenyl)phenylsulfonyl)-butyric acid sodium salt To a solution of the sulfone of Example 37 (450 mg) in THF (5 ml) and ethanol (10 ml) was added N sodium hydroxide (1 ml). After stirring overnight at room temperature the product was filtered: m.p. 215°–218° (d).

EXAMPLE 39

4-(3-(2-(7-Bromoquinolin-2-yl)ethenyl)-6-chlorophenoxy)butyric acid sodium salt

Step 1. Preparation of 3-methoxy-6-chlorotoluene

A solution of 3-methyl-4-chlorophenol (100 g), methyl iodide (200 g) and K$_2$CO$_3$ (150 g) in acetone (500 ml) were refluxed 6 hours, filtered and evaporated to yield the title compound which was used as is in the next step.

Step 2. Preparation of 3-methoxy-6-chlorobenzoic acid

To a solution of the anisole from the previous step (110 g) in t-butanol (500 ml) and H$_2$O (1.5 L) at reflux was added carefully in portions over 5 hours KMnO$_4$ (350 g). The reaction mixture was cooled, NaHSO$_3$ was added, and the mixture was filtered. Most of the t-butanol was removed on a rotary evaporator. Hydrochloric acid (10N) was added until pH 2. The white solid was filtered to yield the title compound which was used as is for the next step.

Step 3. Preparation of 3-methoxy-6-chlorobenzyl-alcohol

To a solution of LiAlH$_4$ (12 g) in THF (1 L) was added dropwise over 1 hour the previous acid (38 g). The reaction mixture was stirred overnight at room temperature and carefully quenched by the addition of H$_2$O (15 ml). To the resulting mixture was then added 10N NaOH (5 ml) and H$_2$O (15 ml). After stirring 1 hour the reaction mixture was filtered and evaporated to yield the title compound which was used as is for the next step.

Step 4. Preparation of 3-methoxy-6-chlorobenzaldehyde

To a stirred solution of the previous alcohol (20 g) in CH$_2$Cl$_2$ (1 L) and powdered 4A molecular sieves (100 g) was added pyridinium chlorochromate (40 g). The mixture was stirred 3 hours at room temperature, 1 liter of 50% ether in hexane was added, and the reaction mixture was filtered. The filtrate was evaporated under vacuo to afford 14 g of the title compound.

PMR (CDCl$_3$) 3.9 (s, 3H), 7.0–7.5 (m, 3H), 10.4 ppm (s, 1H).

Step 5. Preparation of 7-bromo-2-(2-(3-methoxy-6-chlorophenyl)ethenyl)-quinoline A mixture of aldehyde (1.7 g) and 7-bromoquinaldine in acetic anhydride (20 ml) was heated overnight at 140°. The reaction mixture was evaporated. Purification of the residue by flash chromatography using chloroform afforded the title compound which was used as is for the next step.

Step 6. Preparation of 7-bromo-2-(2-(3-hydroxy-6-chlorophenyl)ethenyl)-quinoline To the ether (3.0 g) (Step 5) in chloroform (50 ml) at 0° was added dropwise 1M $BBr_3$ (20 ml). The reaction mixture was stirred 1 hour at room temperature. pH 7 buffer (100 ml) was added. The mixture was extracted with $CHCl_3$ (100 ml) dried and evaporated. The residue was dissolved in methanol (100 ml) and NaOH (20 ml). The mixture was stirred 1 hour at room temperature and evaporated. To the residue $H_2O$ (100 ml) was added. The solution was acidified to pH 1 with HCl and filtered. The yellow solid was suspended in pH 7 buffer (200 ml) stirred 1 hour and filtered.

PMR ($CDCl_3+CD_3SOCD_3$) 6.6 (dd, 1H), 7.0-7.1 (m, 3H), 7.39 (dd, 1H), 7.5-7.56 (m, 2H), 7.85 (d, 1H), 7.95 (d, 1H), 8.02 (d, 1H), 9.1 ppm (s, 1H).

Step 7. Preparation of ethyl 4-(3-(2-(7-bromo-quinolin-2-yl)ethenyl)-6-chlorophenoxy)-butyrate A solution of the phenol (0.6 g), ethyl4-iodobutyrate (1.5 g) and potassium carbonate (1 g) in methylethylketone (15 ml) were refluxed overnight. The reaction mixture was filtered and evaporated. Chromatography of the residue using 20% ethyl acetate in hexane afforded the title compound which was used as is for the next step.

To a solution of the ester (0.35 g) in THF (2 ml) and EtOH (2 ml) was added 2N NaOH (1 ml). The reaction mixture was stirred overnight at room temperature. The product was filtered, washed with EtOH, and dried to yield the title compound m.p. 215°–220°.

EXAMPLE 40

(E)-4-(3-(2-(Quinolin-2-yl)-1-methylethenyl)phenoxy)

A compound of Formula H was prepared.

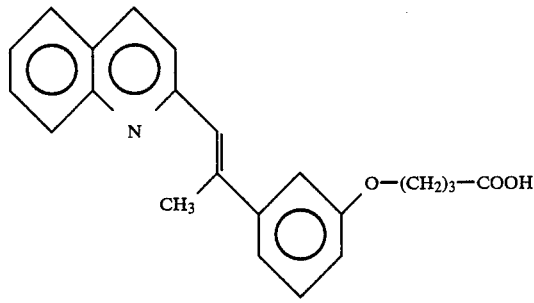

Step 1. Preparation of 1-trimethylsilylmethyl-quinoline

To quinaldine (10 q) in ether (50 ml) at −78° was added dropwise over 30 minutes n-butyllithium (45 ml of 1.6M). The solution was stirred 30 minutes at −50°. To the solution was added dropwise trimethylsilylchloride (9.B ml). The reaction mixture was warmed to room temperature and stirred 3 hours. After quenching with water (0.5 ml). The reaction mixture was filtered on celite and distilled. There was obtained the title quinoline: b p 132° at mm.

Step 2. Preparation of (E)-2-(2-methyl-(3-methoxy-phenyl)ethenyl)quinoline and (Z)-2-(2-methyl-(3-methoxyphenyl)ethenyl)quinoline To a solution of diisopropylamine (3.3 ml) in THF (30 ml) at −78° was added dropwise n-butyl-lithium (15 ml of 1.6 M solution). The resulting solution was stirred at −78° 1 hour. The silyl quinoline (5.0 g) was added dropwise over 10 minutes. After another 10 minutes 3-methoxy-acetophenone was added dropwise. The green solution was stirred 1 hour at −78° then 2 hours at room temperature. The reaction mixture was quenched with water, extracted with ethyl acetate, dried and evaporated. Purification by flash chromatography using 20% to 35% ether in hexane afforded the E isomer, m.p. 82°–83° and the Z isomer, m.p. 70°–82°.

Step 3. Preparation of (E)-2-(2-methyl-(3-hydroxy-phenyl)ethenyl)quinoline

To a solution of the ether (2.2 g) in dichloromethane (100 ml) at −78° was added boron tribromide (17 ml of 1M solution in dichloromethane) and stirred 30 minutes at −78°. The reaction mixture was warmed to room temperature and stirred 3 hours. Methanol (50 ml) was added and the solution was heated at 90°. The resulting yellow paste was dissolved in pH 7 buffer (aq. $NH_4OAc$), extracted with ethylacetate, dried and evaporated. Flash chromatography of the residue using ether/hexane 20 to 25% afforded the title quinoline: m.p. 144°–145° C.

Step 4

A solution of the phenol (1.4 g) methyl ethyl ketone (15 ml), milled potassium carbonate and ethyl-4-iodobutyrate (1.6 g) were refluxed overnight. The carbonate was filtered, and the filtrate was evaporated. The residue was purified by flash chromatography using ether/hexane 20 to 25%. There was obtained the ethyl ester of the title compound. To this ester (1.1 g) in tetrahydrofuran methanol (17 ml) and water (13 ml) was added 2N sodium hydroxide 4 ml. After stirring 4 hours at room temperature, the solution was evaporated to remove organic solvents. The resulting aqueous solution was acidified to pH 4 with 2N HCl and the resulting precipitate filtered to afford the title compound: m.p. 127°–129° C.

EXAMPLE 45

4-(3-(2-(7-Bromoquinolin-2-yl)ethenyl)phenoxy)butyric acid sodium salt

To a solution of the ester of Example 5, Step 2, (15 g) in ethanol (200 ml) and tetrahydrofuran (200 ml) was added 2N NaOH (35 ml). The reaction was stirred at room temperature overnight and the product filtered The solid was stirred for 2 hours at room temperature in ethanol (100 ml) and filtered to give the title compound.

Anal. Calc'd for $C_{21}H_{17}BrNO_3Na$:

Calc.: C, 58.08; H, 3.95; N, 3.23; Br, 18.40;

Found: C, 57.91; H, 4.08; N, 3.18; Br, 18.33.

EXAMPLE 54

Methyl 2-(3-(2-(7-Bromoquinolin-2-yl)ethenyl)phenoxy)-propanoate

To the phenol (Example 35, Step 2) (1 g) in methyl ethyl ketone (20 ml) was added methyl DL-2-bromopropionate (2 g) and $K_2CO_3$ (1 g). The mixture was heated overnight at reflux filtered and evaporated. Flash chromatography of the residue using 10% ethyl acetate in hexane afforded the title compound. Recrystallization from ethyl acetate hexane afforded the title compound: m.p. 101°–102°.

EXAMPLE 55

2-(3-(2-(7-Bromoquinolin-2-yl)ethenyl)phenoxy)propionic acid

To the compound of Example 54 (0.5 g) in THF (10 ml) and ethanol (20 ml) at room temperature was added sodium hydroxide (2N). The reaction mixture was stirred overnight at room temperature. The solution was evaporated under vacuo and then redissolved in H20. To the resulting solution was added acetic acid (1 ml). The yellow solid was filtered to give the title compound.

PMR ($CD_3SOCD_3$): 1.45 (d, 3H), 3.3 (bs, 1H), 3.9 (q, 1H), 6.8 (m, 1H), 7.2–8.0 (m, 7H), 8.15 (d, 1H), 8.30 ppm (d, 1H).

EXAMPLE 56

Ethyl 3-methyl-4-(3-(2-(7-bromoquinolin-2-yl)ethenyl)-phenoxy)butyrate

Step 1. Preparation of 3-methyl-4-(3-formylphenoxy)-buten-2-oic acid ethyl ester A solution of m-hydroxybenzaldehyde (12 g), potassium carbonate (12 g) and 3-methyl-4-bromo-buten2-oic acid ethyl ester in methylethylketone was refluxed overnight. The reaction mixture was filtered. Purification of the residue on a Waters Prep 500 LC using 12% ethyl acetate in hexane afforded the title compound as a 3:2 mixture of cis and trans isomers.

Step 2. Preparation of ethyl 3-methyl-4-(3-formyl-phenoxy)butanoate

The olefin (5 g) from Step 1 was hydrogenated using $PtO_2$ (100 mg) in ethyl acetate in a Parr hydrogenator at 20 psi for 3 hours. The catalyst was filtered and the filtrate evaporated. Purification of the residue by chromatography on a Water Prep 500 LC ($SiO_2$) using 12% ethyl acetate in hexane as an eluant afforded the title compound.

PMR ($CDCl_3$): 1.2 (d, 3H), 1.3 (t, 3H), 2.2–2.8 (m, 3H), 3.9 (d, 2H), 4.2 (q, 2H), 7.0–7.6 (m, 4H), 9.9 ppm (s, 1H).

Step 3

A solution of aldehyde, Step 2, (1.8 g) and 7-bromoquinaldine in acetic anhydride were heated for 48 hours at 130°. The reaction mixture was evaporated and purified by chromatography on a Waters Prep 500 using 5% ethyl acetate in toluene to yield the title compound.

PMR ($CDCl_3$): 1.1 (d, 2H), 1.2 (t, 3H), 2.20 (dd, 1H), 2.40 (m, 1H), 2.6 (dd, 1H), 3.98 (d, 2H), 4.15 (q, 2H), 6.9 (m, 1H), 7.2–7.8 (m, 8H), 8.16 (d, 1H), 8.24 ppm (d, 1H).

EXAMPLE 57

Preparation of 3-methyl-4-(2-(7-bromoquinolin-2-yl)-ethenyl)phenoxy)-butyric acid sodium salt To a solution of the compound of Example 56 (1.5 g) in ethanol (50 ml) was added 2N NaOH (4 ml). The solution was stirred 2 hours at room temperature and 1 hour at 50°. The ethanol was evaporated. The residue was applied on an XAD-8 column using $H_2O$. Elution with $H_2O$ (1 L) removed the salts. The compound was then eluted with ethanol (1 L). Evaporation of the ethanol afforded the title compound: m.p. 197°–203°.

PMR ($CD_3OD$): 1.1 (d, 3H), 2.12 (m, 1H), 2.4 (m, 2H), 3.7–4.0 (m, 2H), 6 9 (m, 1H), 7.2–7.4 (m, 4H), 7.6–7.9 (m, 4H, B.15 (d, 1H), 8.26 ppm (d, 1H).

EXAMPLE 59

5-[3- [2-(7-Bromoquinolin-2-yl)ethenyl]phenoxy propyl]-1H-tetrazole

A mixture of the nitrile of Example 58 (1.0 g) in DMF (7 ml) in the presence of ammonium chloride (544 mg) and sodium azide (663 mg) was heated at 125° C. for 18 hours. Then more ammonium chloride (270 mg) and sodium azide (330 mg) were added to the warm mixture and stirred for 20 additional hours. The mixture was cooled to room temperature, poured into $H_2O$ (100 ml) and the formed yellow solid was filtered and purified on a column of flash silica gel using an eluant a mixture of dichloromethane-ethanol (100:3) to afford a yellow foam (264 mg) which was swished overnight in $Et_2O$ (20 ml) to afford the title compound.

Mass spectra showed a molecular ion at m/e 435 ($^{79}Br$)

PMR ($CDCl_3$+MeOD): 2.35 (quint., 2H), 3.2 (t, 2H), 4.15 (t, 2H), 6 87 (dd, 1H), 7.15–7.45 (m, 4H), 7.55–7.85 (m, 4H, 8.17 (d, 1H), 8.25 (s, 1H).

EXAMPLE 60

Methyl 5-(3-[2-(7-Bromoquinolin-2-yl)ethenyl]phenoxy)-3,3-dimethyl pentanoate

Step 1. Preparation of methyl 4-carboxy-3,3-dimethyl butanoate

A solution of 3,3-dimethylglutaric anhydride (14.2 g) in MeOH (50 ml) was refluxed overnight and then cooled to room temperature and evaporated to dryness to give the title product as a colorless oil.

PMR ($CDCl_3$) 1.15 (s, 6H), 2.5 (s, 4H), 3.7 (s, 3H), 11.0 (s(b),1H).

Step 2. Preparation of methyl 5-hydroxy-3,3-dimethyl pentanoate

To a solution of acid (5 g) in anhydrous THF (50 ml) was added dropwise a solution of 0.98M $BH_3$ in THF (35 ml). The reaction mixture was stirred at room temperature for 3 hours Then the reaction mixture was coevaporated with MeOH (3 x 200 ml) to give a colorless liquid of the title compound PMR ($CDCl_3$) 1.05 (s, 6H), 1.65 (t, 2H), 2.25 (s(b), 1H), 2.3 (s, 2H), 3.65 (s, 3H), 3.75 (t, 2H).

Step 3. Preparation of methyl 5-methanesulfonyl-3,3-dimethyl pentanoate

A solution of alcohol (1.6 g) in $CH_2Cl_2$ (20 ml) and triethylamine (2.8 ml) was cooled to 0° C. and methanesulfonyl chloride (1 ml) was added slowly. The mixture was stirred at room temperature for 2 hours and then transferred to a separatory funnel, washed with water, dried and evaporated to give the title product as an orange oil.

PMR ($CDCl_3$) 1.1 (s, 6H), 1.85 (t, 2H), 2.25 (s, 2H), 3.0 (s, 3H), 3.65 (s, 3H), 4.3 (t, 2H).

Step 4. Preparation of methyl 5-iodo-3,3-dimethyl pentanoate

A solution of mesylate (2.4 g) in MEK (16 ml) in the presence of NaI (3 g) was refluxed for 3 hours The mixture was cooled to 0° C., filtered and filtrate evaporated. The residue was diluted with $CH_2Cl_2$, washed consecutively with $H_2O$, 5% aqueous sodium thiosulfate, dried and evaporated to give the title product.

PMR ($CDCl_3$) 1.0 (s, 6H), 2.0 (t, 2H), 2.25 (s, 2H), 3.0–3.3 (m, 2H), 3.7 (s, 3H).

A solution of phenol (Example 35, Step 2) (978 mg) and alkyl iodide (1 22 g) in MEK (15 ml) was refluxed for 24 hours in the presence of milled $K_2CO_3$ (1.24 g). The mixture was then cooled to 0° C., filtered and filtrate evaporated to give a yellow oil which was chromatographed on flash silica gel column using hexane-ethyl acetate (5:1) as eluant to afford an oil which after trituration in hexane-ether afforded the title product as yellow solid: m.p. 50°–52° C.

EXAMPLE 61

5-(3-[2-(7-Bromoquinolin-2-yl)ethenyl]phenoxy)3,3-dimethyl pentanoic acid sodium salt A solution of the ester (Example 60) (468 mg) in THF (2 ml), MeOH (3 ml), and 2N NaOH (1.5 ml) was stirred for 3 days at room temperature. Then the mixture was evaporated to dryness and passed through a column of neutral resin XAD-8 using $H_2O$ (300 ml), followed by EtOH (500 ml) as eluants. Evaporation of the ethanol afforded a solid which was triturated in $Et_2O$ and filtered to provide the title compound m.p. 190°–195° C.(d).

PMR (MeOD) 1.18 (s, 6H), 1..95 (t, 2H), 2.23 (s, 2H), 4.15 (t, 2H), 6.9 (dd, 1H), 7.1–7.35 (m, 4H), 7.5–7.85 (m, 4H), 8.08 (s, 1H), 8 18 (d, 1H).

EXAMPLE 71

5-(1-(3-(2-(7-chloroquinolin-2-yl)ethyl)phenoxy)-tetrazole

STEP 1. Preparation of 7-chloro-2-(2-(3-hydroxy-phenyl)ethenyl)quinoline

Using the procedure described in example 35, Step 1 and 2, but using 7-chloroquinaldine instead of 7-bromoquinaldine there was obtained the title compound which was used as such for the next step.

STEP 2. Preparation of 2-(3-(2-(7-chloroquinolin-2-yl)ethenyl)phenoxy)-propanonitrile A mixture of the phenol from Step 1 (150 g), (+) 2-bromo-propionitrile and milled potassium carbonate in methylethyl ketone (1 L) was refluxed for 8 hrs. The reaction mixture was cooled and filtered. Recrystallization from ethyl acetate/hexane afforded the title compound m.p. 118°–120°.

STEP 3.

5-(1-(3-(2-(7-chloroquinolin-2-yl)ethenyl)-phenoxy)ethyl)tetrazole

A mixture of the propanonitrile (110 g) from Step 2 and tri-butyltin azide (120 g) was heated at 130° for 3 hours. The residue was dissolved in $CH_2Cl_2$ (1 L) on a steam bath. This solution was added to a mixture of diethylether (2 L), ethanol (100 ml) and acetic acid (10 ml). This mixture was evaporated under vacuo to approximately 300 ml. The residue was triturated with ether (1.5 L), ethyl acetate (600 ml) and filtered. The yellow solid was dissolved in 2 N NaOH (150 ml) and $H_2O$ (1 L). The aqueous solution was extracted with ethyl acetate (100 ml). The aqueous solution was then acidified with AcOH (100 ml) in ethyl acetate (100 ml). The mixture was stirred 30 min and filtered to give title compound. m.p. 100°–103°.

Anal Calcd for $C_{20}H_{16}ClN_5O \cdot H_2O$ C 60.68, H 4.54, N 17.70, Cl 8.95

Found: C 60.38, H 4.75, N 17.61, Cl 8.85

EXAMPLE 72

(+)-2-(3-(2-(7-Chloroquinolin-2-yl)ethenyl)phenoxy) propanoic acid

Sodium hydride (960 mg, 40 mmol) was added in two portions to an ice-cold solution of 3-(2-(7-chloroquinolin-2-yl)ethenyl)phenol (Example 71, Step 1) (2.815 g, 10 mmol) in dry tetrahydrofuran (50 mL) under dry nitrogen. When hydrogen evolution had abated, a solution of L-2-chloropropanoic acid (2.17 g, 20 mL) in dry tetrahydrofuran (50 mL) was added dropwise and with stirring. The gelatinous suspension was heated under reflux, during which it became initially a fine yellow suspension, and later a paler more voluminous precipitate replaced the yellow solid.

The reaction mixture was treated with ethyl acetate, and ammonium acetate buffer was added together with enough acetic acid to maintain a pH of 6.5–7.0 during the ensuing anhydrous magnesium sulphate, and evaporated onto Merck silica gel (15 g). The solid was placed on top of a column of silica gel (150 g), and the column was eluted at first with 2% ethanol in toluene, and then with 1:10:100 acetic acid/ethanol/toluene. After a small fraction of recovered starting material, the pure product was eluted. Evaporation of the eluate yielded a glassy foam, which crystallized on swishing 50.4° (c 0.995 in acetone).

Calcd. for $C_{20}H_{16}ClNO_3$: C 67.90, H 4.56, Cl 10.02, N 3.96; found: C 67.33, H 4.62, Cl 9.85, N 3.91.

EXAMPLE 73

(−)-2-(3-(-(7-Chloroquinolin-2-yl)ethenyl)phenoxy)-propanoic acid

Substituting D-2-chloropropanoic acid for L-2-propanoic acid in the above procedure for example 72, provided the title compound in approximately the same yield as its enantiomer, mp 103°–105° C., $[\alpha]_D$ −50.9° (c 0.995 in acetone)

Calcd. for $C_{20}H_{16}ClNO_3$; C 67.90, H 4.52, Cl 10.02, N 3.96: found; C 67.90, H 4.52, Cl 10.24, N 3.97.

EXAMPLE 74

(−)-2-(3-(2-(7-Chloroquinolin-2-yl)ethenyl)phenoxy)-propanoamide (+)-2-(3-(2-(7-Chloroquinolin-2-yl)ethenyl)phenoxy)propanoic acid from Example 72 (2.372 g, 6.71 mmol) was dissolved in methylene chloride (40 mL) containing triethylamine (1.87 mL, 12.5 mmol), and ethyl chloroformate (710 μL, 7.38 mmol) in methylene chloride (20 mL) was added dropwise at −15° C. with stirring. The mixture was stirred for a further 20 minutes at −15° C., and then it was poured into methylene chloride (125 mL) that had been saturated with ammonia at 0° C. The reaction mixture was stirred for a few minutes, and then poured into ice-water The mixture was filtered, and the filtrate was separated. Evaporation of the methylene chloride layer gave more solid, and the two fractions were combined and recrystallized from acetonitrile to give the title product, mp 195°-197° C., $[\alpha]_D$ −9.8° (c 0.515 in dimethylformamide).

Calcd. for $C_{20}H_{17}ClN_2O_2$: C 68.09, H 4.86, Cl 10.04, N 7.94: found; C 67.35, H 4.86, Cl 10.32, N 8.06

EXAMPLE 75

(+)-2-(3-(2-(7-Chloroquinolin-2-yl)ethenyl)phenoxy)-propanoamide

Using (−)-2-(3-(2-(7-Chloroquinolin-2--Yl)ethenyl)phenoxy)propanoic acid from Example 73 in place of the (+)-enantiomer in the procedure of example 74, the title compound was obtained, mp 195°-197° C., .35° (c 0.54 in dimethylformamide).

Calcd. for $C_{20}H_{17}ClN_2O_2$; C 68.09, H 4.86, Cl 10.04: found; C 68.29, H 4.98, Cl 8.03, N 9.63.

EXAMPLE 76

(+)-2-(3-(2-(7-Chloroquinolin-2-yl)ethenyl)phenoxy)-propanenitrile

A mixture of (−)-2-(3-(2-(7-chloroquinolin-2yl)ethenyl)phenoxy)propanoamide (1.317 g, 3.73 mmol), from Example 74, dioxane (25 mL), and pyridine (2.8 mL, 22.4 mmol) was cooled in a bath at −15° C. until freezing began, and at that point trifluoroacetic anhydride (0.580 mL, 4.11 mmol) was added and the reaction was transferred to an ice-bath. After 15 minutes, the mixture was poured onto ice, and the crude product was isolated by column chromatography on merck silica eluted with 1:2 ethyl acetate/hexane to afford pure nitrile, mp 147°-148° C. (ex acetonitrile), $[\alpha]_D$+139.2° (c 0.99 in dichloromethane)

Calcd. for $C_{20}H_{15}ClN_2O$; C 71.75, H 4.52, Cl 10.59, N 8.37: found; C 71.65, H 4.63, Cl 10.01, N 8.28.

EXAMPLE 77

(−)-2-(3-(2-(7-Chloroquinolin-2-yl)ethenyl)phenoxy)-propanenitrile

Using (+)-2-(3-(2-(7-Chloroquinolin-2-yl)ethenyl)phenoxy)propanoamide from Example 75 in place of the (+)-enantiomer in example 76, gave the title compound, mp 147°-149° C. (ex acetonitrile), D -134.4° (c 0.98 in dichloromethane).

Calcd for $C_{20}H_{15}ClN_2O$; C 71.75, H 4.52, Cl 10.59, N 8.37: found; C 71.88, H 4.61, Cl 10.79, N 8.16.

EXAMPLE 78

(+)-5-(1-(3-(2-(7-Chloroquinolin-2-yl)ethenyl)phenoxy)ethyl)tetrazole

A mixture of (+)-2-(3-(2-(7-chloroquinolin-2yl)ethenyl)phenoxy)propanenitrile from Example 76 (1.31 g, 3.91 mmol) and tributyltin hydride (1.95 g, 5.87 mmol) was heated under argon, in an oil-bath at 120° C. for 2 hours. The gum was stirred with methylene chloride (20 mL), and the solution was evaporated onto Merck silica gel (15 g). The solid was placed on a column of silica gel (150 g) and the column was eluted with 1:20:100 acetic acid/dioxane/toluene. The isolated solid was suspended in methanol (10 mL) and dissolved in the hot by the addition of 10% ammonium hydroxide. After filtration, the solution was acidified with acetic acid to give a solid containing methanol. Recrystallization of this solid from ethanol gave the product containing the latter solvent, mp 149°-151° C. dec., +62.0° (c 1.02 in methanol).

Calcd for $C_{20}H_{16}ClN_5O.1/3$ $C_2H_5OH$: C 63.13, H 4.62, Cl 9.02, N 17.82; found: C 63.01, H 4.57, Cl 9.55, N 18.38.

EXAMPLE 79

(−)-5-(1-(3-(2-(7-Chloroquinolin-2-yl)ethenyl)phenoxy)-ethyl)tetrazole

Replacing the (+)-nitrile with the (−)-enantiomer from Example 77 in the procedure of Example 78 gave the title compound as a solid containing ethanol, mp 148°-150° C. dec., $[\alpha]_D$ −58.2° (c 1.03 in methanol).

Calcd. for $C_{20}H_{16}ClN_5O$. 2/3 $C_2H_5$.1/3$H_2O$: C 61.81, H 5.02, Cl 8.55, N 16.90; found: C 61.84, H 4.81, Cl 8.43, N 17.26.

EXAMPLE 80

4-(3-(2-(7-bromoquinolin-2-yl)ethynyl)phenoxy)-butanoic acid sodium salt

A compound of Formula J was prepared.

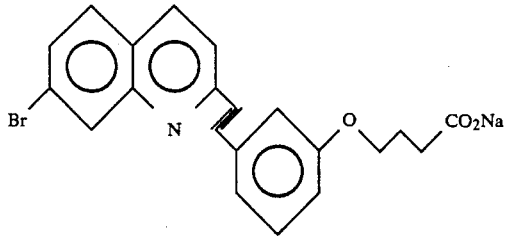

STEP 1. Preparation of 3-((1 or 2)-bromo-2-(7-bromo-quinolin-2-yl)ethenyl)phenoxyacetate To the compound of Example 35, step 1 (3 g) in acetic acid (9 mL) was added dropwise a solution of bromine (0.46 mL) in acetic acid (1 mL). During the course of the reaction more acetic acid (4 mL) was added and the mixture was stirred at 120° C. for 1 hour. The reaction mixture was cooled to room temperature and treated as follows. The liquors were decanted and the residue saved for further treatment. The liquors were diluted with $H_2O$ and the pH was brought to 7 with 10N NaOH and extracted with ethyl acetate to give after usual transformation sample A. The saved residue was triturated with H2O and suspended in H2O and ethyl acetate. 10N NaOH was added portionwise with vigourous stirring until pH 7 was reached. The organic phase was saved and treated the usual way to give sample B which was combined with sample A and reacetylated with acetic anhydride (10 mL) at room temperature for 30 min. The reaction mixture was poured into pH 7 buffer solution, extracted with CH2Cl2, dried and evaporated to give an oil which was chromatographed on flash silica gel column using toluene as eluant to afford the title product as colorless oil.

PMN (CDCl3) δ: 2.35 (s, 3H), 7.1–7.3 (m, 1H), 7.45 (t, 1H), 7.6–7.75 (m, 4H), 8.0 (d, 1H), 8.18 (d, 1H), 8.28 (s, 1H), 8.35 (s, 1H).

STEP 2. Preparation of 3-(2-(7-bromoquinolin-2-yl)-ethynyl)phenoxyacetate

To a solution of the vinyl bromide from step 1 (1 g) in THF (10 mL) was added DBU (1,8-diazabicyclo [5.4.0]undec-7-ene) (0.84 mL) and the mixture was refluxed for 4 hours. The mixture was cooled to room temperature, poured into pH 7 buffer solution and extracted with ethyl acetate. The organic layers were dried, filtered and filtrate evaporated to afford an oil which was reacetylated as in step 1 and treated as the same to afford an oil which was chromatographed on flash silica gel column using toluene-ethyl acetate (10:0:3) to give the title product as yellow solid: m.p. 126°–128° C.

STEP 3 Preparation of 3-(2-(7-bromoquinolin-2-yl)-ethynyl)phenol

To a solution of the acetate from Step 2 (550 mg) in THF (5 mL) and methanol (5 mL) was added milled potassium carbonate (414 mg) and the mixture stirred at room temperature for 2.5 hours. The mixture was poured into pH 7 buffer solution and extracted with ethyl acetate. The organic layer was dried, filtered and filtrate evaporated to afford the title product as yellow solid: m.p. 197°–199° C.

STEP 4. Preparation of ethyl 4-(3-(2-(7-bromo-quinolin-2-yl)ethenyl)phenoxy)-butanoate A solution of the phenol from Step 3 (470 mg), methyl ethyl ketone (10 mL), milled potassium carbonate (600 mg) and ethyl 4-iodo-butyrate (421 mg) was refluxed overnight The solids were filtered, and the filtrate was evaporated. The residue was purified by flash chromatography using toluene-ethyl acetate (10:0:3) to afford the title product as yellow solid: m.p. 61°–63° C.

Anal. Calcd for C23H20BrNO3: Calc.: C, 63.02; H, 4.60; N, 3.20; Br, 18.23 Found: C, 62.86; H, 4.60; N, 3.06; Br, 18.16

STEP 5, 4-(3-(2-(7-bromoquinolin-2-yl)ethynyl)-phenoxy)-butanoic acid sodium salt To a solution of the ethyl ester from Step 4 (380 mg) in THF (4 mL) and EtOH (2 mL) was added 2N NaOH (0.65 mL) and the mixture was stirred overnight at room temperature. The reaction mixture was evaporated to dryness and passed through a neutral XAD-8 resin, eluting with H2O and then with EtOH, to afford the title compound as a white solid: m.p. 250° C. (d).

PMR (CD3OD) δ: 1.2 (quint., 2H), 1.48 (t, 2H), 3.18 (t, 2H), 6.15 (dd, 1H), 6.32 (d, 2H), 6.45 (t, 1H), 6.8–6.9 (m, 2H), 9.0 (d, 1H), 7 28 (d, 1H), 6.48 (d, 1H).

EXAMPLE 81

Methyl (D,L) 2-(3-(2-(7-bromoquinolin-2-yl)ethynyl)-phenoxy)-propanoate

A compound of Formula K was prepared.

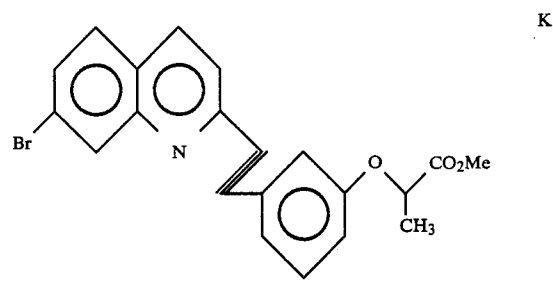

K

To the phenol from Example 80, Step 3 (520 mg) in methyl ethyl ketone (10 mL) was added methyl DL-2-bromopropanoate (0.23 mL). The mixture was refluxed overnight, filtered and evaporated. Flash chromatography of the residue using toluene-ethyl acetate (10:0:3) afforded the title compound as a white solid m.p. 96°–97° C.

Anal for C21H16BrNO3: Calc. C, 61.47; H, 3.93; N, 3.41; Br, 19.48 Found: C, 61.48; H, 4.05; N, 3.32; Br, 19.50

EXAMPLE 82

(D,L) 2-(3-(2-(7-bromoquinolin-2-yl)ethynyl)phenoxy)-propanoic acid sodium salt

A compound of Formula L was prepared.

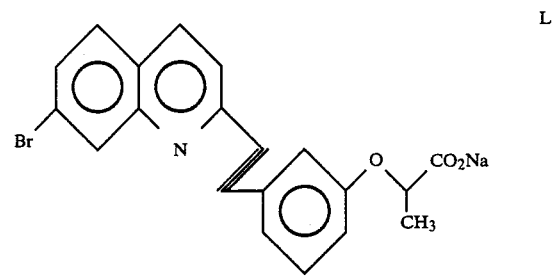

L

To the compound of Example 81 (0.5 g) in EtOH (12 mL) was added 10N NaOH (0.18 mL) and the mixture stirred overnight at room temperature. The mixture was evaporated to dryness and passed through a neutral XAD-8 resin column, eluting subsequently with H2O and ethanol, to afford the title compound as white solid.

Anal. for C20H13BrNO3Na-2 H2O: Calc.: C, 52.88; H, 3.77; N, 3.08 Found: C, 52.58; H, 3.95; N, 3.02

EXAMPLE 83

(Z)-(D,L)-2-(3-(2-(7-chloroquinolin-2-yl)-1-methylethenyl)phenoxy)propanoic acid sodium salt A compound of Formula M was prepared.

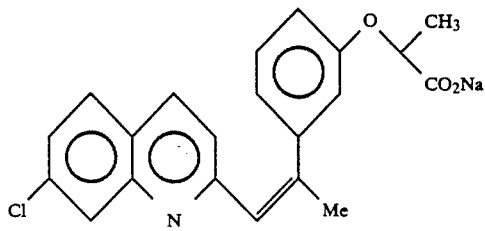

M

STEP 1. Preparation of 7-chloro-2-trimethylsilylmethyl quinoline

Using the same procedure as for Example 40, Step 1, but replacing quinaldine by 7-chloroquinaldine, the title quinoline was obtained after distillation b.p. 95° C. at 0.6 mm Hg.

STEP 2. Preparation of (Z)-7-chloro-2-(2-methyl-2-(3-methoxyphenyl)ethenyl)-quinoline and (E)-7-chloro-2-(2-methyl-2-(3-methoxyphenyl)ethyl)-quinoline Using the same procedure as for Example 40, Step 2 but replacing 2-trimethylsilylmethyl quinoline by 7-chloro-2-trimethylsilylmethyl quinoline (Step 1), after purification by flash chromatography using toluene-ethyl acetate (10:0.1) there was obtained the Z isomer, m.p. 65°-70° C. and the E isomer (used in Example 84, Step 1), m.p. 82°-84° C.

STEP 3. Preparation of (Z)-7-Chloro-2-(2-methyl-2-(3-hydroxyphenyl)ethenyl)quinoline Using the same procedure as in Example 40, Step 3 but replacing (E)-Z-[2-methyl-(3-methoxyphenyl)ethenyl]quinoline by (Z)-7-chloro-2-[2-methyl(3-methoxyphenyl)ethenyl]quinoline (from Step 2) afforded the title compound as a crude solid.

PMR (CDCl$_3$): 2.28 (s, 3H), 6.65 (d, 1H), 6.72 (d(b), 2H), 6.85 (d, 2H), 7.2 (t, 1H), 7.38 (dd, 1H), 7.55 (d, 1H), 7.7 (d, 1H), 7.9 (s, 1H)

STEP 4. Preparation of methyl (Z)-(D,L)-2-(3-(2-(7-chloroquinolin-2-yl)-1-methylethenyl)phenoxy)propanoate To the phenol from Step 3 (281 mg) in methyl ethyl ketone (5 mL) was added methyl (D,L)-2-bromopropanoate (185 mg). The mixture was refluxed overnight, filtered and evaporated. Flash chromatography of the residue using toluene-ethyl acetate (10:0.3) afforded the title compound as a white solid: m.p. 82°-84° C.

STEP 5. (Z)-(D,L)-2-(3-(2-(7-chloroquinolin-2-yl)-1-methylethenyl)phenoxy)propanoic acid sodium salt A solution of the methyl ester from Step 4 (381 mg) in EtOH (7 mL) was warmed to 50° C. and 10N NaOH (0.2 mL) was added and the mixture stirred at 50° C. for 2 hours. The reaction mixture was evaporated to dryness and the residue was passed through a column of neutral XAD-8 resin, eluting subsequently with H$_2$O and EtOH, to afford the title compound as a white foam (365 mg, 94%).

Anal. for C$_{21}$H$_{17}$ClNO$_3$Na.1½ H$_2$O: Calc.: C, 60.50; H, 4.84; N, 3.36; Cl, 8.51; Na, 5.52 Found: C, 60.92; H, 4.88; N, 3.53; Cl, 8.34; Na, 5.32

EXAMPLE 84

(E)-(D,L)-2-(3-(2-(7-Chloroquinolin-2-yl)-1-methylethenyl)phenoxy)propanoic acid sodium salt A compound of Formula N was prepared.

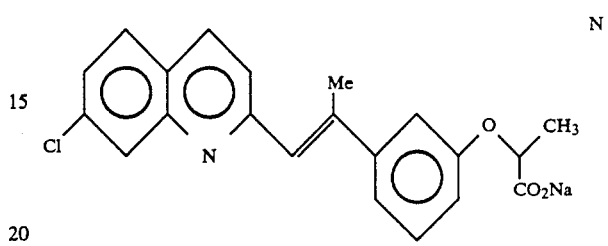

N

STEP 1. Preparation of (E)-7-Chloro-2-[2-methyl-2-(3-hydroxyphenyl)ethenyl]quinoline Using the same procedure as in Example 40, Step 3 but replacing (E)-2-(2-methyl-2-(3-methoxyphenyl)ethenyl)quinoline by (E)-7-chloro-2-(2-methyl-2-(3-methoxyphenyl)ethenyl)quinoline isolated as shown in Example 83, Step 2, there was obtained the title compound as a crude oil.

PMR (CDCl$_3$) δ: 2.65 (s, 3H), 6.85 (dd, 1H), 7.95 (s, 1H), 7.0-7.1 (m, 2H), 7.15-7.30 (m, 1H), 7.40-7.50 (m, 2H), 7.73 (d,1H), 8.1 (d, 1H), 8.18 (s, 1H).

STEP 2. Preparation of methyl (E)-(D,L)-2-(3-(2-(7-chloroquinolin-2-yl)-1-methylethenyl)phenoxy)propanoate To the phenol from Step 1 (535 mg) in methyl ethyl ketone (10 mL) was added methyl (D,L)-2-bromopropanoate (363 mg) and treated as in Example 83, Step 4 to afford the title compound as an oil.

PMN (CDCl$_3$) δ: 1.65 (d, 3H), 2.65 (d, 3H), 3.8 (s, 3H), 4,85 (g, 1H), 6.85 (dd, 1H), 7.95 (s, 1H), 7.15-7.5 (m, 5H), 7.7 (d, 1H), 8.08 (d, 1H), 8.a (s, 1H).

STEP 3. (E)-(D,L)-2-(3-(2-(7-Chloroquinolin-2-yl)-1-methylethenyl)phenoxy)propanoic acid sodium salt A solution of the methyl ester from Step 2 (624 mg) in EtOH (10 mL) was warmed to 50° C. and 10N NaOH (0.33 mL) was added and stirred at 50° C. for 2 hours. The mixture was treated as in Example 83, Step 5 to afford the title compound as foam.

Anal. for C$_{21}$H$_{17}$ClNO$_3$Na.1½ H$_2$O: Calc.: C, 60.50; H, 4.84; N, 3.36; Na, 5.52 Found: C, 60,77; H, 4.84; N, 3.22; Na, 5.71

EXAMPLE 85

2-(3-(7-bromoquinolin-2-ylmethoxy)phenoxy)-propanoic acid

A compound of Formula O was prepared.

EXAMPLE 86

5-(1-(3-(2-(7-chloroquinolin-2-yl)cyclopropyl)phenoxy)ethyl)-1H-tetrazole

A compound of Formula P was prepared.

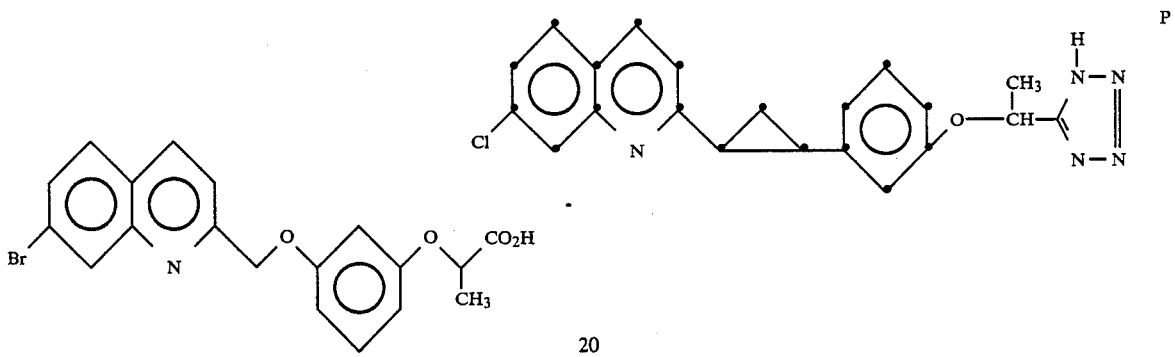

Preparation of methyl 2-(3-hydroxyphenoxy)-propanoate

A mixture of resorcinol (11.0 g), methyl 2-bromopropanoate (20 g), potassium carbonate (27.6 g) and methyl ethyl ketone (120 mL) was heated under reflux for 5 hours. The reaction mixture was filtered, evaporated and the residue was separated by chromatography. Elution with 1:3 ethyl acetate/hexane afforded the desired product.

PMR (CDCl$_3$) δ: 1.5 (d, 3H), 3.7 (s, 3H), 4.8 (q, 1H), 6.1 (s, 1H), 6.3–6.6 (m, 3H), 7.0 p.p.m. (m, 1H).

STEP 2. Preparation of (7-bromo-quinolin-2-yl)methylbromide

A mixture of 220 g 7-bromoquinaldine, 180 g N-bromosuccinimide and 1 g dibenzoylperoxide in CCl$_4$ (1 L) was illuminated with a 275 W sun lamp at reflux for 12 hours. The reaction mixture was cooled and directly chromatographed on 2 kg silica gel. Elution with toluene afforded the title compound which was used as is for the next step.

STEP 3. Preparation of methyl 2-(3-(7-bromoquinolin-2-ylmethoxy)phenoxy)propanoate A mixture of the quinolinyl methyl bromide (903 mg) (Step 2), the phenolic ester (Step 1), potassium carbonate (828 mg) and ethyl methyl ketone (15 mL) was stirred under reflux for 3 hours. The reaction mixture was filtered and evaporated. Flash chromatography of the residue using 1:20 ethyl acetate/toluene afforded the title compound.

PMR (CDCl$_3$) δ: 1.8 (d, 3H), 3.75 (s, 3H), 4.75 (q, 1H), 5.25 (s, 2H), 6.4 (d, 1H), 6.5–6.65 (m, 2H), 7.1 (t, 1H), 7.6–7.7 (m, 3H), 8.15 (d, 1H), 8.25 p.p.m. (d, 1H).

STEP 4. 2-(3-(7-bromoquinolin-2-ylmethoxy)phenoxy)-propanoic acid

A mixture of the ester (Step 3) (861 mg), methanol (13 mL) and 5N sodium hydroxide (0.54 mL) was heated under reflux for 2 hours. The reaction mixture was evaporated to approximately 4 mL and acidified to pH 4.5 with HCl (0.5N). This gave a gum which crystallized in methanol to give the title compound. mp 178°

Anal calc'd for C$_{20}$H$_{18}$BrNO$_4$ C 57.71, H 4.36, N 3.36, Br 19.20 Found: C 57.62, H 4.58, N 3.31, Br 19.55

STEP 1. Preparation of (E)-3-(2-(7-chloroquinolin-2-yl)ethenyl)anisole 7.1 mL of 3-methoxybenzaldehyde (58 mmoles), 9.953 g of 7-chloroquinaldine (56 mmoles) and 50 mL of acetic anhydride were mixed together and heated at 110° C. for 16 hours. After hydrolysis on ice, the product was extracted with ethyl acetate, washed with 5% sodium bicarbonate and brine and partially purified by flash chromatography using 10% ethyl acetate in hexane. Recrystallisation from ether: hexane yielded the title compound.

$^1$H NMR (CD$_3$COCD$_3$) δ: 3.9 (3H, s), 6.95 (1H, ddd), 7.25–7.4 (3H, m), 7.45–7.55 (2H, m), 7.80–8.05 (4H, m), 8.35 (1H, d).

STEP 2. Preparation of 3-(2-(7-chloroquinolin-2-yl)cyclopropyl)anisole

To trimethylsulfonium iodide (9.98 g, 2. eg.) in 60 mL of THF was added, at −10° C., 15 mL of n-BuLi (1.6M in hexane). The temperature was raised to room temperature for 2 hours. Then, at −10° C., the alkene (from Step 1) (7.037 g, 23.8 mmoles) in 30 mL of THF was added. After 30 minutes at −10° C., the reaction mixture was stirred overnight at room temperature. Hydrolysis with 25% aqueous NH$_4$OAc, extractions with ethyl acetate and flash chromatography with toluene yielded the desired product.

$^1$H NMR (CD$_3$COCD$_3$) δ: 1.57 (1H, m), 1.91 (1H, m), 2.50–2.70 (2H, m) 3.77 (3H, s), 6.70–6.82 (3H, m), 7.20 (1H, dd), 7.45–7.55 (2H, m), 7.87–7.94 (2H, m), 8.21 (1H, d).

STEP 3. Preparation of 3-(2-(7-chloroquinolin-2-yl)cyclopropyl)phenol

To the cyclopropylanisole (from Step 2) (1.478 g, 4.77 mmoles) in 20 mL CH$_2$Cl$_2$ at −10° C. was added AlCl$_3$ (1.915 g, 3 eg.) and ethanethiol (1.2 mL, 3.3 eg.). The temperature was raised to 0° C. for 2 hours. Then 10% HCl and THF: EtOAc (1:1) were added and the mixture was stirred and heated until the resulting gum was solubilized. After separation of the phases and extractions with THF:EtOAc (1:1), flash chromatography using 5% EtOAc in toluene yielded the title phenol.

Anal calc'd for C$_{18}$H$_{14}$ClNO: C 73.10; H 4.77; H, 4.74; Cl 11.99 Found: C 72.90, 72.79; H, 4.72, 4.73; N, 4.66, 4.73; Cl 11.85, 11.76.

STEP 4. Preparation of 2-(3-(2-(7-chloroquinolin-2-yl)cyclopropyl)phenoxy)-propanenitrile A mixture of phenol (from Step 3) (1.060 g, 3.58 mmoles), 2-bromopropionitrile (370 μL, 1.2 eg.), $K_2CO_3$ (752 mg, 1.5 eg.) and methyl ethyl ketone (15 mL) was heated under reflux for 20 hours. Then, ethyl acetate was added and the salts were removed by filtration on Elite. Flash chromatography of the residue with toluene afforded the title compound.

$^1$H NMR ($CD_3COCD_3$) δ: 1.64 (1H, m), 1.77 (3H, d), 1.95 (1H, m), 2.55-2.73 (2H, m), 5.36 (1H, q), 6.90-7.00 (3H, m), 7.30 (1H, dd), 7.45-7.60 (2H, m), 7.90-7.95 (2H, m), 8.22 (1H, d).

STEP 5.
5-(1-(3-(2-(7-chloroquinolin-2-yl)cyclopropyl)phenoxy)ethyl)-1H-tetrazole A mixture of tributyltin azide (1.603 g, 1.5 eg.) and the nitrile (Step 4) (1.115 g, 3.20 mmoles) was heated at 120° C. for 4 hours. Flash chromatography of this reaction mixture using EtOAc: toluene AcOH 20:80:1 and 40:60:1 yielded the title compound.

$^1$H NMR ($CD_3COCD_3$) δ: 1.58 (1H, m), 1.78 (3H, d), 1.92 (1H, m), 2.50-2.68 (2H, m), 6.01 (1H, q), 6.80-6.94 (3H, m), 7.21 (1H, dd), 7.46-7.58 (2H, m), 7.90-7.96 (2H, m), 8.23 (1H, d).

The leukotriene antagonist properties of compounds of the present invention were evaluated using the following assay.

Guinea-Pig Ileum Preparation for Evaluation of Antagonists of Leukotriene D4 and Other Mediators Tissue—Sections of ileum were taken from male Hartley strain guinea pigs (Charles River, U.S.A.) 300 to 500 g which were sacrificed by a blow to the head and exsanguinated. Terminal ileum was removed, cleaned with warm Tyrode's solution and then divided into segments of approximately 1.5–2.0 in each. The segments of ileum were then mounted under 1 g tension in a 20 mL organ bath containing 10 mL of Tyrode's solution with the following composition (mM): NaCl, 137; KCl, 2.7; $MgSO_4$, $7H_2O$, 0.8; $CaCl_2$, 1.8; $NaH_2PO_4$, 0.42; $NaHCO_3$, 11.9; Dextrose, 5.6. The bathing solution was continuously aerated with 95% $O_2$ and 5% $CO_2$ and bath temperature was maintained at 37° C. The beta adrenoceptor blocker, timolol (0.5 μg/mL) and the antimuscarinic agent atropine (1.0 μM) were present in the Tyrodeμs solution. Isometric tension changes were recorded using Grass FTO3 force displacement transducers (Grass Instrument G., Quincy, Mass.) connected to a Beckman Type R Dynograph. In order to wash the tissue, the bath solution was automatically aspirated and replaced with a constant volume (10 mL) of fresh solution by means of timer controlled solenoid valves.

Antagonist Testing:

After the tissues were stable a standard dose of $LTD_4$ (0.3 ng/mL) was repeatedly added to the bath every 4-5 minutes (min contact, 30 sec wash, 3 min rest) until a consistent response was obtained (minimum of 4 responses). Following each addition of $LTD_4$ the tissue was washed with Tyrode's solution until baseline tension was re-established. After consistent responses were obtained the tissues were used to screen compounds.

Usually, 10 μL of a 10 mg/mL solution of the compound to be tested was added to the bath 30 secs prior to the addition of $LTD_4$. The compound and $LTD_4$ remained in contact with the tissue until the maximum tension was developed (1 min) after which the tissue was washed repeatedly until the baseline was re-established. Percent inhibition relative to the immediately preceding control response was calculated for each dose of test compound. If the compound was active (greater than 50% inhibition), then tests were performed with 10 fold serial dilutions until inhibition was less than 50%. Provided the response was inhibited by less than 20%, the tissue was used immediately to evaluate another compound; when the response was inhibited by greater than 20%, cycles of $LTD_4$ alone were added until a consistent response was re-established.

The results for $LTD_4$ binding were determined by the method of S. S. Pong and R. N. DeHaven, Proc. Nat. Acad. Sci. U.S.A., 80, 7415–7419 (1983).

In Table I are presented data indicating the $LTD_4$ antagonist activity of compounds of the present invention as compared to a reference compound which has only a one-atom bridge between the quinoline and phenyl rings.

The drug concentration in the $LTD_4$ binding assay for the numbered examples are the $IC_{50}$ values. The $LTD_4$ binding activity of these ranges from at least 14 (Ex. 85) to at least 214 (Ex. 71) times greater than the reference compound. The actual differences are even greater since an $IC_{50}$ was not obtained for the reference compound.

The ability of the compounds of the numbered examples to inhibit $LTD_4$ contractions of the guinea Pig ileum ranges from about 20 (Ex. 85) to over 1000 (Ex. 71) times greater then the reference compound. It can be concluded that the two-atom bridge of this invention results in compounds with greatly increased leukotriene antagonist activity.

TABLE I

| Compound | G.P. ILEUM ASSAY % INHIBITION OF $LTD_4$ INDUCED CONTRACTIONS AT DRUG CONC. (μg/mL) | | | | | $LTD_4$ BINDING ASSAY | |
|---|---|---|---|---|---|---|---|
| | 10 | 1 | 0.1 | 0.01 | 0.001 | DRUG CONC. | % $LTD_4$ BOUND |
| 7-Chloro-quinolin-2-yl REFERENCE 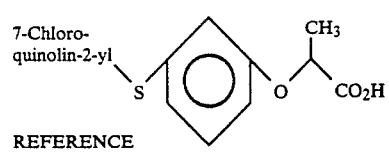 | 89 | 27 | — | — | — | $3 \times 10^{-6}$ M | 76% |

TABLE I-continued

| Compound | G.P. ILEUM ASSAY % INHIBITION OF LTD₄ INDUCED CONTRACTIONS AT DRUG CONC. (μg/mL) | | | | | LTD₄ BINDING ASSAY | |
|---|---|---|---|---|---|---|---|
| | 10 | 1 | 0.1 | 0.01 | 0.001 | DRUG CONC. | % LTD₄ BOUND |
| 7-Chloro-quinolin-2-yl (EXAMPLE 67) [structure: vinyl-phenyl-O-CH(CH₃)-CO₂H] | 94 | 97 | 95 | 94 | 38 | $1.5 \times 10^{-8}$ M | 50% |
| 7-Chloro-quinolin-2-yl (EXAMPLE 71) [structure with tetrazole] | 97 | 98 | 100 | 92 | 67 | $1.4 \times 10^{-8}$ M | 50% |
| 7-Bromo-quinolin-2-yl (EXAMPLE 82) [structure: vinyl-phenyl-O-CH(CH₃)-CO₂Na] | 97 | 98 | 94 | 91 | 50 | $9.6 \times 10^{-8}$ M | 50% |
| 7-Bromo-quinolin-2-yl (EXAMPLE 85) [structure: CH₂-O-phenyl-O-CH(CH₃)-CO₂H] | 100 | 93 | 57 | 10 | 0 | $2.2 \times 10^{-8}$ M | 50% |
| 7-Chloro-quinolin-2-yl (EXAMPLE 86) [cyclopropyl-phenyl with tetrazole] | 94 | 96 | 87 | 37 | — | $1.3 \times 10^{-8}$ M | 50% |

What is claimed is:

1. A compound of the formula:

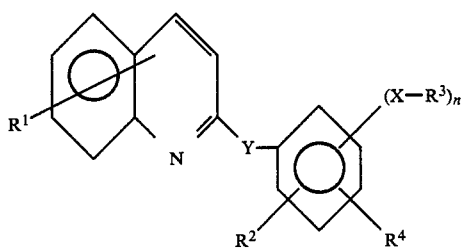

I wherein:
$R^1$ is H, halogen, $C_1$-$C_8$ alkyl, $C_2$-$C_8$ alkenyl, $C_2$-$C_8$ alkynyl, —$CF_3$, —$OR^2$, $SR^2$, —CHO, —$COOR^2$, —(C=O)$R^2$, —C(OH)$R^2R^2$, —CN, substituted or unsubstituted phenyl, substituted or unsubstituted benzyl, or substituted or unsubstituted phenethyl;
$R^2$ is independently H, $C_1$-$C_8$ alkyl, $C_2$-$C_8$ alkenyl, $C_2$-$C_8$ alkynyl, or —$CF_3$;
$R^3$ is independently $(CR^2R^2)_m$—Q;
$R^4$ is independently H, halogen, —CN, —$OR^2$, —$SR^2$, or $C_1$-$C_8$ alkyl;
$R^9$ is independently —$OR^{10}$, —$SR^{10}$, or —$NR^{10}R^{10}$;
$R^{10}$ is independently H, $C_1$-$C_6$ alkyl, —(C=O)$R^{11}$, unsubstituted phenyl or unsubstituted benzyl;
$R^{11}$ is independently H, $C_1$-$C_8$ alkyl, $C_2$-$C_8$ alkenyl, $C_2$-$C_8$ alkynyl, —$CF_3$, or unsubstituted phenyl, benzyl, or phenethyl;
m is independently 1-4;
n is independently 1 or 2;
Q is independently —$COOR^2$ or tetrazole;
X is independently O, S, —SO, or —$SO^2$;
Y is independently —$(CR^2=CR^2)_n$—, or —(-C≡C)$_n$—;
substituted phenyl, benzyl, and phenethyl mean 1-2 substituents selected from $C_1$-$C_6$ alkyl, $R^9$, $NO_2$, $SCF_3$, halogen, —$COR^9$, CN, $CF_3$, and —CHO;
with the proviso that when $R^4$ is on the carbon adjacent to X it is not OH, SH, or $NHR^2$;
and the pharmaceutically acceptable salts thereof.

2. A compound of claim 1 of the Formula Ia:

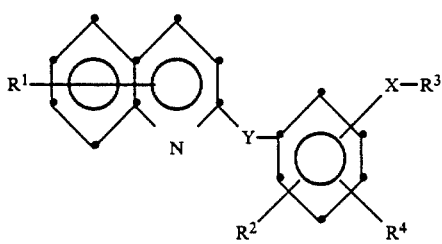

wherein:
R¹ is H, halogen, C₁-C₈ alkyl, C₂-C₈ alkenyl, C₂-C₈ alkynyl, —CF₃, —OR², —SR², —CHO, —COOR², —(C=O)R², —C(OH)R²R², —CN, —NO₂, substituted or unsubstituted phenyl, substituted or unsubstituted benzyl, or substituted or unsubstituted phenethyl;
and the pharmaceutically acceptable salts thereof.

3. A compound of claim 1 of the Formula Ib:

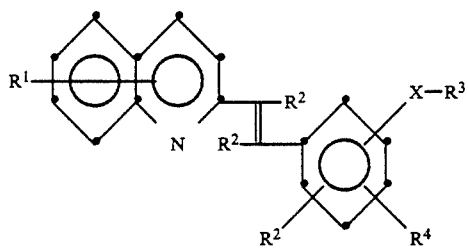

wherein:
R¹ is H, halogen, CH₃, —CF₃, or SCF₃; and
R² is H, C₁-C₃ alkyl, C₂-C₃ alkenyl, or —CF₃;
and the pharmaceutically acceptable salts thereof.

4. A compound of claim 1 of the Formula Ic:

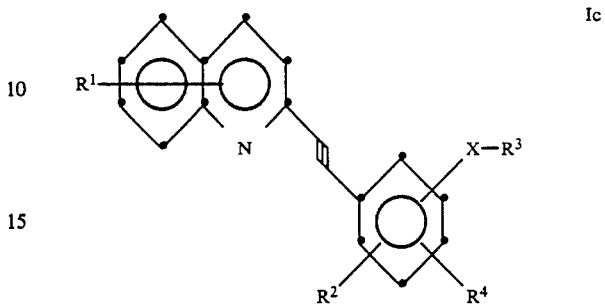

wherein:
R¹ is H, halogen, CH₃, C₂-C₃ alkenyl, —CF₃, or SCF₃;
R² is H, C₁-C₃ alkyl, C₂-C₃ alkenyl, or —CF₃;
and the pharmaceutically acceptable salts thereof.

5. A compound of claim 1 which is a compound of Formula E:

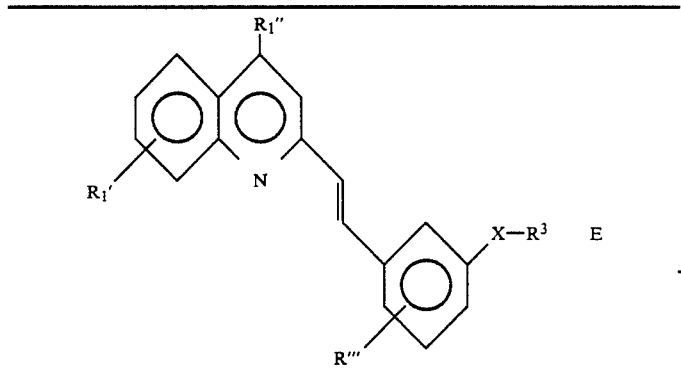

wherein:

| $R_1'$ | $R_1''$ | R''' | X—R³ |
|---|---|---|---|
| 5-Cl | H | H | —O(CH₂)₃—CO₂Et |
| 6-Cl | H | H | —O(CH₂)₃—CO₂Et |
| 7-Cl | H | H | —O(CH₂)₃—CO₂Et |
| 6-Br | H | H | —O(CH₂)₃—CO₂Et |
| 7-Br | H | H | —O(CH₂)₃—CO₂Et |
| 7-F | H | H | —O(CH₂)₃—CO₂Et |
| 6-F | H | H | —O(CH₂)₃—CO₂Et |
| 5-CF₃ | H | H | —O(CH₂)₃—CO₂Et |
| 7-CF₃ | H | H | —O(CH₂)₃—CO₂Et |
| 6-CH₃ | H | H | —O(CH₂)₃—CO₂Et |
| H | H | H | —OCH₂CO₂Me |
| H | H | H | —SCH₂CO₂Me |
| H | H | 5'-OCH₂CO₂Me | —OCH₂CO₂Me |
| 6-Br | H | H | —OCH₂CO₂CH₃ |
| 6-F | H | H | —CH₂CO₂CH₃ |
| 6-Cl | H | H | —OCH₂CO₂CH₃ |
| 6-Me | H | H | —OCH₂CO₂CH₃ |
| H | H | H | —OCH₂CO₂H |
| H | H | 5'-propyl | —OCH₂CO₂CH₃ |
| H | H | 5'-propyl | —OCH₂COOH |
| H | H | H | —NHCOCOOEt |

-continued

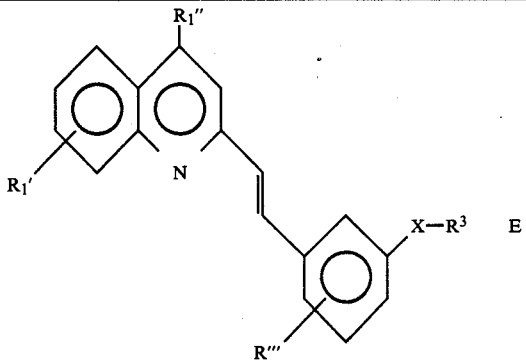

E wherein:

| $R_1'$ | $R_1''$ | $R'''$ | $X-R^3$ |
|---|---|---|---|
| 7-Br | H | H | $-OCH_2CO_2CH_3$ |
| 7-Br | H | H | $-OCH_2CO_2H$ |
| 7-S-butyl | H | H | $-OCH_2CO_2CH_3$ |
| H | propyl | H | $-O(CH_2)_3COOH$ |
| 6-(1-hexenyl) | H | H | $-OCH_2CO_2CH_3$ |
| H | H | H | $-O(CH_2)_3-CO_2H$ |
| 8-butyl | H | H | $-O(CH_2)_3-CO_2Et$ |
| H | H | 5'-O-$(CH_2)_3$-COOH | $-O(CH_2)_3-COOH$ |
| 7-Br | H | H | $-S-(CH_2)_3-COOEt$ |
| 7-Br | H | H | $-S-(CH_2)_3-CO_2Na$ |
| 7-Br | H | H | $-SO_2-(CH_2)_3-CO_2Et$ |
| 7-Br | H | H | $-SO_2-(CH_2)_3-CO_2Na$ |
| 7-Br | H | 6'-Cl | $-O-(CH_2)_3-CO_2Na$ |
| 7-Br | H | H | $-O-CH(CH_3)CO_2Me$ |
| 7-Br | H | H | $-O-CH(CH_3)CO_2H$ |
| 7-Br | H | H | $-O-CH_2-CH(CH_3)$<br>$\quad\quad\quad\quad\quad\mid$<br>$\quad\quad\quad\quad\quad CH_2CO_2Et$ |
| 7-Br | H | H | $-O-CH_2-CH(CH_3)$<br>$\quad\quad\quad\quad\quad\mid$<br>$\quad\quad\quad\quad\quad CH_2CO_2Na$ |
| 7-Br | H | H | $-O-(CH_2)_3$-tetrazole |
| 7-Br | H | H | $-O-(CH_2)_2-C-(CH_3)_2$<br>$\quad\quad\quad\quad\quad\quad\mid$<br>$\quad\quad\quad\quad\quad\quad CH_2CO_2Me$ |
| 7-Br | H | H | $-O-(CH_2)_2-C-(CH_3)_2$<br>$\quad\quad\quad\quad\quad\quad\mid$<br>$\quad\quad\quad\quad\quad\quad CH_2CO_2Na$ |
| 7-$CF_3$ | H | H | $-O-C-CO_2H$<br>$\quad\quad\mid$<br>$\quad\quad CH_3$ |
| 7-Br | H | H | $-O-CH_2$-tetrazole |
| 7-Br | H | H | $-O-CH-CO_2Na$<br>$\quad\quad\mid$<br>$\quad\quad CH_2CH_3$ |
| 7-F | H | H | $-O-CH-CO_2Na$<br>$\quad\quad\mid$<br>$\quad\quad CH_3$ |
| 7-Cl | H | H | $-O-CH-CO_2H$<br>$\quad\quad\mid$<br>$\quad\quad CH_3$ |
| 7-Br | H | H | $-O-CH$-tetrazole<br>$\quad\mid$<br>$\quad CH_3$ |
| 7-Cl | H | H | $(+,-)-O-CH$-tetrazole<br>$\quad\quad\quad\mid$<br>$\quad\quad\quad CH_3$ |

-continued

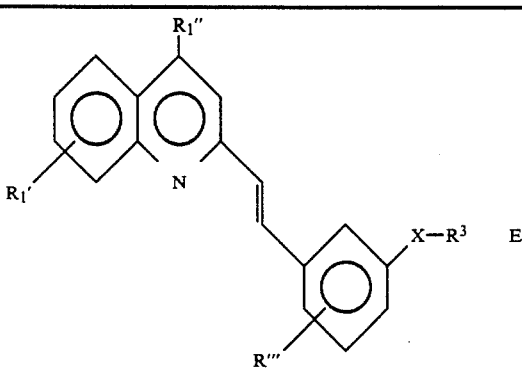

wherein:

| $R_1'$ | $R_1''$ | $R'''$ | $X-R^3$ |
|---|---|---|---|
| 7-Cl | H | H | (+)-O—CH(CH$_3$)—COOH |
| 7-Cl | H | H | (−)-O—CH(CH$_3$)—COOH |
| 7-Cl | H | H | (+)-O—CH(CH$_3$)-tetrazole |
| 7-Cl | H | H | (−)-O—CH(CH$_3$)-tetrazole |

6. A compound of claim 5 wherein $R_1''$ is H, $R'''$ is H, $R_1'$ is in the 7 position, and wherein $R_1'$ and $X-R^3$ are as follows:

| $R_1'$ | $X-R^3$ |
|---|---|
| Br | —O—CH(CH$_3$)CO$_2$H |
| Cl | —O—CH(CH$_3$)—CO$_2$H |
| Br | —O—CH(CH$_3$)-tetrazole |
| Cl | (+,−)-O—CH(CH$_3$)-tetrazole |
| Cl | (+)-O—CH(CH$_3$)—COOH |
| Cl | (−)-O—CH(CH$_3$)—COOH |
| Cl | (+)-O—CH(CH$_3$)-tetrazole |
| Cl | (−)-O—CH(CH$_3$)-tetrazole |

7. A compound of claim 1 which is a compound of Formula F:

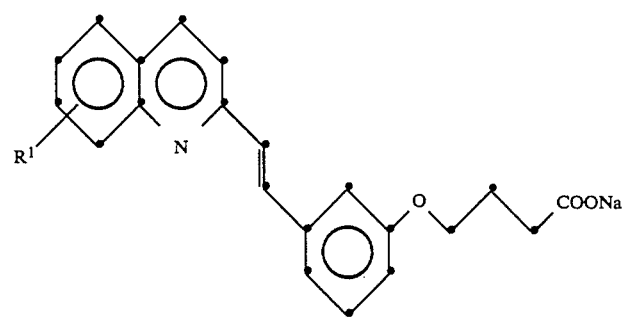

wherein:

$R_1$ is 5—Cl; 6—Cl; 7—Cl; 6—Br; 7—Br; 7—$CF_3$; 5—$CF_3$; 7—F; 6—Me; or 6—F.

8. A compound of claim 1 of Formula G:

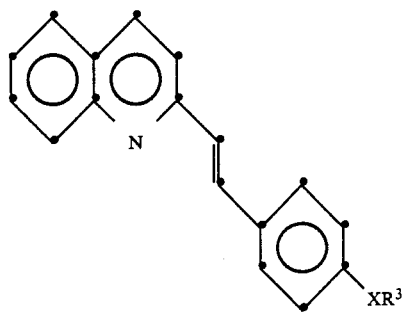

wherein $XR^3$ is $OCH_2CO_2Me$.

9. A compound of claim 1 which is:
(E)-4-(3-(2-(quinolin-2-yl)-1-methylethenyl)phenoxy)butyric acid;
Methyl (D,L) 2-(3-(2-(7-bromoquinolin-2-yl)ethynyl)phenoxy)propanoate;
(E)-(D,L)-2-(3-(2-(7-chloroquinolin-2-yl)-1-methylethenyl)phenoxy)propanoic acid sodium salt;
4-(3-(2-(7-bromoqiunolin-2-yl)ethynyl)phenoxy)-butanoic acid sodium salt;
(D,L) 2-(3-(2-(7-bromoquinolin-2-yl)ethynyl)phenoxy)propanoic acid sodium salt; or
(Z)-(D,L) 2-(3-(2-(7-chloroquinolin-2-yl)methylethenyl)phenoxy)propanoic acid sodium salt.

* * * * *

UNITED STATES PATENT AND TRADEMARK OFFICE
CERTIFICATE OF CORRECTION

PATENT NO. : 4,962,203

DATED : 10/9/90

INVENTOR(S) : Robert N. Young, Serge Leger, Robert Zamboni, Haydn W. R. Williams and Richard Frenette It is certified that error appears in the above-identified patent and that said Letters Patent is hereby corrected as shown below: Title page Amend the assignee's name to read:
-- Merck Frosst Canada, Inc. --

Claim 5, col. 52, last line, delete the compound:
"H       H       H       -NHCOCOOEt"

Signed and Sealed this

Twelfth Day of May, 1992

*Attest:*

DOUGLAS B. COMER

*Attesting Officer*      *Acting Commissioner of Patents and Trademarks*